US012767706B2

(12) United States Patent
Di Mambro et al.

(10) Patent No.: US 12,767,706 B2
(45) Date of Patent: Oct. 20, 2026

(54) HUMANISED ANTIBODIES AGAINST PATHOGENIC FUNGI

(71) Applicant: DIATHEVA S.R.L., Cartoceto (IT)

(72) Inventors: Tomas Di Mambro, Urbino (IT); Tania Vanzolini, Pesaro (IT); Mauro Magnani, Urbino (IT)

(73) Assignee: DIATHEVA S.R.L., Cartoceto (IT)

(*) Notice: Subject to any disclaimer, the term of this patent is extended or adjusted under 35 U.S.C. 154(b) by 582 days.

(21) Appl. No.: 18/251,298

(22) PCT Filed: Nov. 2, 2021

(86) PCT No.: PCT/EP2021/080372
§ 371 (c)(1),
(2) Date: May 1, 2023

(87) PCT Pub. No.: WO2022/096455
PCT Pub. Date: May 12, 2022

(65) Prior Publication Data

US 2023/0406912 A1 Dec. 21, 2023

(30) Foreign Application Priority Data

Nov. 5, 2020 (IT) ........................ 102020000026398

(51) Int. Cl.
*C07K 16/14* (2006.01)
*A61K 39/395* (2006.01)
*A61K 45/06* (2006.01)
*A61P 31/10* (2006.01)

(52) U.S. Cl.
CPC ........ *C07K 16/14* (2013.01); *A61K 39/39575* (2013.01); *A61K 45/06* (2013.01); *A61P 31/10* (2018.01); *C07K 2317/24* (2013.01)

(58) Field of Classification Search
CPC ................ C07K 16/14; C07K 2317/24; A61K 39/39575; A61K 45/06; A61K 2039/505; A61K 2300/00; A61K 39/395; A61P 31/10
See application file for complete search history.

(56) References Cited

U.S. PATENT DOCUMENTS 7,893,219 B2 2/2011 Cassone et al.

FOREIGN PATENT DOCUMENTS

WO 2006030318 A2 3/2006
WO WO-2011035205 A2 * 3/2011 .............. A61P 31/10
WO WO-2017004563 A1 * 1/2017 ............. C07K 16/14

OTHER PUBLICATIONS

Tevyashova, A., Korolev, A., Trenin, A. et al. New conjugates of polyene macrolide amphotericin B with benzoxaboroles: synthesis and properties. J Antibiot 69, 549-560 (2016). (Year: 2016).*
Capodicasa C, Chiani P, Bromuro C, De Bernardis F, Catellani M, Palma AS, Liu Y, Feizi T, Cassone A, Benvenuto E, Torosantucci A. Plant production of anti-β-glucan antibodies for immunotherapy of fungal infections in humans. Plant Biotechnol J. Sep. 2011;9(7):776-87. (Year: 2011).*
Abbott WM, Damschroder MM, Lowe DC. Current approaches to fine mapping of antigen-antibody interactions. Immunology. Aug. 2014;142(4):526-35. (Year: 2014).*
Jespersen MC, Mahajan S, Peters B, Nielsen M, Marcatili P. Antibody Specific B-Cell Epitope Predictions: Leveraging Information From Antibody-Antigen Protein Complexes. Front Immunol. Feb. 26, 2019;10:298. (Year: 2019).*
Lin et al. Improved affinity of a chicken single-chain antibody to avian infectious bronchitis virus by site-directed mutagenesis of complementarity-determinig region H3. African J Biotech, 2011, 10(79): 18294-18302. (Year: 2011).*
Matveev et al. Novel mouse monoclonal antibodies specifically recognizing β-(1→3)-D-glucan antigen. PLoS One. Apr. 25, 2019;14(4):e0215535. (Year: 2019).*
Bugli Francesca et al., "Human Monoclonal Antibody-Based Therapy in the Treatment of Invasive Candidiasis", Clinical & Developmental Immunology, Jan. 1, 2013, pp. 1-9, vol. 2013.
Di Mambro Tomas et al., "A new humanized antibody is effective against pathogenic fungi in vitro", Scientific Reports—Nature Portfolio, Published Sep. 30, 2021, 17 pages.
Di Mambro Tomas et al., "The Yin and Yang of Current Antifungal Therapeutic Strategies: How We Harness Our Natural Defenses?", Frontiers in Pharmacology, Feb. 5, 2019, 11 pages, vol. 10.
Perfect John R., "The antifungal pipeline: a reality check", Nature Reviews Drug Discovery, May 12, 2017, pp. 603-616, vol. 16, No. 9.
Torosantucci Antonella et al., "A novel glyco-conjugate vaccine against fungal pathogens", Journal of Experimental Medicine, Sep. 1, 2005, pp. 597-606, vol. 202, No. 5, Rockefeller University Press.
International Search Report for PCT/EP2021/080372 mailed Feb. 3, 2022, 5 pages.
Written Opinion of the ISA for PCT/EP2021/080372, mailed Feb. 3, 2022, 8 pages.

* cited by examiner

*Primary Examiner* — Julie Wu
*Assistant Examiner* — Amber K Faust
(74) *Attorney, Agent, or Firm* — Silvia Salvadori, P.C.; Silvia Salvadori

(57) ABSTRACT

The present invention relates to humanised antibody molecules having specificity for β-1,3 glucans and compositions comprising the same. The present invention also relates to the therapeutic uses of the antibody molecules, wherein said use is in the treatment or prophylaxis of fungal infections. It is further claimed a synergistic combination of a) at least one humanised antibody which has specificity for β-1,3 glucans and b) one or more antifungal agents for use in the treatment or prophylaxis of infections of human cells.

18 Claims, 15 Drawing Sheets

Specification includes a Sequence Listing.

```
                                                <---------------------------FR1-IMGT--------------------------><--------CDR1-IMGT------>
                                                  L  Q  Q  S  G  A  E  L  M  K  P  G  A  S  V  K  I  S  C  K  A  T  G  Y  T  L  S  S  Y  W
                              Query_1        1  CTGCAGCAGTCTGGCGCTGAGCTGATGAAGCCTGGGGCCTCAGTGAAGATATCCTGCAAGGCTACTGGCTACACACTCAGTAGCTACTGG  90
V  96.8% (276/285)  IGHV1-9*01      10  ..............A.................................C.T........................T...C.G........  99
                                                  L  Q  Q  S  G  A  E  L  M  K  P  G  A  S  V  K  L  S  C  K  A  T  G  Y  T  F  T  G  Y  W
V  90.2% (257/285)  IGHV1-63*02     10  ..............A.........G.A.G.......A.T...........G............G....A.....CT...C..A.......  99
V  89.8% (256/285)  IGHV1-55*01     10  .........C....G........TG.............T...........G............T..........CT...CC.........  99
V  89.5% (255/285)  IGHV1-56*01     10  ..............AC........G...G.........T........................C.......T..CT...CC...C.....  99
V  89.5% (255/285)  IGHV1-77*01     10  ...A..........A.........G.............T........................T..........CT...C.GA.....AT  99
V  89.1% (254/285)  IGHV1-63*01     10  ..............A.........G.A.G.......A.T...........G............T....A.....CT...C..A.......  99
V  88.8% (253/285)  IGHV1-54*02     10  ..............A.........G.A.G.......A.T.........G.G............T....A...G.CT...C..AT....T.  99
V  88.8% (253/285)  IGHV1-56*02     10  ..............AC........G...G.........T........................C..........CT...CC...C.....  99
V  88.8% (253/285)  IGHV1S61*01     10  .........C....T........TG.......................C.G............T..........TT...CC.........  99
V  88.4% (252/285)  IGHV1-66*01     10  ..............AC........G.............T........................T.........GCT...CA.......AT  99

                                                <--------------------FR2-IMGT--------------------><--------CDR2-IMGT------><--------------
                                                  L  E  W  V  K  Q  R  P  G  H  G  L  E  W  I  G  E  I  L  P  G  S  G  S  T  N  Y  N  E  K
                              Query_1       91  CTAGAGTGGGTAAAGCAGAGGCCTGGACATGGCCTTGAGTGGATTGGAGAGATTTTACCTGGAAGTGGTAGTACTAACTACAATGAGAAG  180
V  96.8% (276/285)  IGHV1-9*01     100  A.........................................................................................  189
                                                  I  E  W  V  K  Q  R  P  G  H  G  L  E  W  I  G  E  I  L  P  G  S  G  S  T  N  Y  N  E  K
V  90.2% (257/285)  IGHV1-63*02    100  A..GT.............................................T....AC.....G.....TA....................  189
V  89.8% (256/285)  IGHV1-55*01    100  A..ACC.....G.................A....................T....AT....T............................  189
V  89.5% (255/285)  IGHV1-56*01    100  A.GC.........GA..............G..........................T.................T.T..T..........  189
V  89.5% (255/285)  IGHV1-77*01    100  A..A.C.....G.................G..................A.....GGT.................T...............  189
V  89.1% (254/285)  IGHV1-63*01    100  A..GT....C........................................T....AC.....G.....TA....................  189
V  88.8% (253/285)  IGHV1-54*02    100  A............................G...................T...AAT............G.....................  189
V  88.8% (253/285)  IGHV1-56*02    100  A.GC.........GA..............G..........................T.................T.T..T.........A  189
V  88.8% (253/285)  IGHV1S61*01    100  A..A.C.....G.................A..................A.T....AT....T..A.........................  189
V  88.4% (252/285)  IGHV1-66*01    100  A..C.C.....G.................G..A...............TG.....AT............A.....G..............  189

                                                -------------------------------------FR3-IMGT------------------------------------------
                                                  F  K  G  K  A  T  F  T  A  D  T  S  S  N  T  A  Y  M  Q  L  S  S  L  T  S  E  D  S  A  V
                              Query_1      181  TTCAAGGGCAAGGCCACATTCACTGCAGATACATCCTCCAACACAGCCTACATGCAACTCAGCAGCCTGACATCTGAGGACTCTGCCGTC  270
V  96.8% (276/285)  IGHV1-9*01     190  ........................................................................A..............A..  279
                                                  F  K  G  K  A  T  F  T  A  D  T  S  S  N  T  A  Y  M  Q  L  S  S  L  T  T  E  D  S  A  I
V  90.2% (257/285)  IGHV1-63*02    190  ..................C.G........C..........G...............G..............................A..  279
V  89.8% (256/285)  IGHV1-55*01    190  ......A...........C.G...T....C..........G...............G.............................G...  279
V  89.5% (255/285)  IGHV1-56*01    190  ..................C.G...T....C..........G...............G.............................G...  279
V  89.5% (255/285)  IGHV1-77*01    190  ..................C.G........C.A........G...............G..............................A..  279
V  89.1% (254/285)  IGHV1-63*01    190  ..................C.G........C.A........G...............GT.............................A..  279
V  88.8% (253/285)  IGHV1-54*02    190  ..............A...C.G........C.A........................G.............................G...  279
V  88.8% (253/285)  IGHV1-56*02    190  ..................C.G..TT....C..........G...............G.....................A.......G...  279
V  88.8% (253/285)  IGHV1S61*01    190  ......A...........C.G...T....C..........G...............G.....................C.......G...  279
V  88.4% (252/285)  IGHV1-66*01    190  ..................C.G..G.....C..........G..T............G..........A..................G...  279

                                                --------><--------CDR3-IMGT--------><-----------FR4-IMGT----------->
                                                  Y  Y  C  A  R  E  G  W  Y  F  D  V  W  G  A  G  T  T  V  T  V  S  S
                              Query_1      271  TATTACTGTGCAAGAGAGGGTTGGTACTTCGATGTCTGGGGCGCAGGGACCACGGTCACCGTCTCCTCA  339
V  96.8% (276/285)  IGHV1-9*01     280  ...............------------------------------------------------------  294
                                                  Y  Y  C  A  R
V  90.2% (257/285)  IGHV1-63*02    280  ...............------------------------------------------------------  294
V  89.8% (256/285)  IGHV1-55*01    280  ...............------------------------------------------------------  294
V  89.5% (255/285)  IGHV1-56*01    280  ....T..........------------------------------------------------------  294
V  89.5% (255/285)  IGHV1-77*01    280  ....T..........------------------------------------------------------  294
V  89.1% (254/285)  IGHV1-63*01    280  ...............------------------------------------------------------  294
V  88.8% (253/285)  IGHV1-54*02    280  ....T..........------------------------------------------------------  294
V  88.8% (253/285)  IGHV1-56*02    280  ....T..........------------------------------------------------------  294
V  88.8% (253/285)  IGHV1S61*01    280  .....T.........------------------------------------------------------  294
V  88.4% (252/285)  IGHV1-66*01    280  ...............------------------------------------------------------  294
J  100.0% (48/48)   IGHJ1*01         5  ---------------------................................................  52
J  97.9% (47/48)    IGHJ1*02         5  ---------------------.........................................T......  52
J  97.9% (47/48)    IGHJ1*03         5  ---------------------.....................A..........................  52
```

Fig. 1

```
VH2G8 patent   ---------    ctgcagcagtctggcgctgagctgatgaagcctggggcctcagtgaagata   51
IGHV1-9*01     caggttcag    ctgcagcagtctggagctgagctgatgaagcctggggcctcagtgaagctt   60
IGHV1-56*02    caggtccag    ctgcagcagtctggacctgagctggtgaggcctggggcttcagtgaagata   60
IGHV1-63*02    caggtccag    ctgcagcagtctggagctgagctggtaaggcctgggacttcagtgaagatg   60
IGHV1-63*01    caggtccag    ctgcagcagtctggagctgagctggtaaggcctgggacttcagtgaagatg   60
IGHV1-54*02    caggtccag    ctgcagcagtctggagctgagctggtaaggcctgggacttcagtgaaggtg   60
IGHV1-55*01    caggtccaa    ctgcagcagcctggggctgagcttgtgaagcctggggcttcagtgaagatg   60
IGHV1S61*01    caggtccaa    ctgcagcagcctggtgctgagcttgtgaagcctggggcctcagtgaagctg   60
IGHV1-77*01    caggtccag    ctgaagcagtctggagctgagctggtgaagcctggggcttcagtgaagata   60
IGHV1-66*01    caggtccag    ctgcagcagtctggacctgagctggtgaagcctggggcttcagtgaagata   60
                            *** ***** ****  *******  * * ******* * ********* *

VH2G8 patent    tcctgcaaggctactggctacacactcagtagctactggctagagtgggtaaagcagagg   111
IGHV1-9*01     tcctgcaaggctactggctacacattcactggctactggatagagtgggtaaagcagagg   120
IGHV1-56*02    tcctgcaaggctcctggctacaccttcaccagccactggatgcagtgggtaagacagagg   120
IGHV1-63*02    tcctgcaaggctgctggatacaccttcactaactactggataggttgggtaaagcagagg   120
IGHV1-63*01    tcctgcaaggcttctggatacaccttcactaactactggataggttgggcaaagcagagg   120
IGHV1-54*02    tcctgcaaggcttctggatacgccttcactaattacttgatagagtgggtaaagcagagg   120
IGHV1-55*01    tcctgcaaggcttctggctacaccttcaccagctactggataacctgggtgaagcagagg   120
IGHV1S61*01    tcctgcaaggcttctggctacactttcaccagctactggataaactgggtgaagcagagg   120
IGHV1-77*01    tcctgcaaggcttctggctacaccttcactgactactatataaactgggtgaagcagagg   120
IGHV1-66*01    tcctgcaaggcttctggctacagcttcacaagctactatatacactgggtgaagcagagg   120
               ************ **** ***     ***       ***    *    ****  *  ******

VH2G8 patent   cctggacatggccttgagtggattggagagattttacctggaagtggtagtactaactac   171
IGHV1-9*01     cctggacatggccttgagtggattggagagattttacctggaagtggtagtactaactac   180
IGHV1-56*02    cctggacagggccttgagtggattggagagatttttcctggaagtggtagtacttattat   180
IGHV1-63*02    cctggacatggccttgagtggattggagatatttaccctggaggtggttatactaactac   180
IGHV1-63*01    cctggacatggccttgagtggattggagatatttaccctggaggtggttatactaactac   180
IGHV1-54*02    cctggacagggccttgagtggattggagtgattaatcctggaagtggtggtactaactac   180
IGHV1-55*01    cctggacaaggccttgagtggattggagatatttatcctggtagtggtagtactaactac   180
IGHV1S61*01    cctggacaaggccttgagtggattggaaatatttatcctggtagtagtagtactaactac   180
IGHV1-77*01    cctggacagggccttgagtggattggaaagattggtcctggaagtggtagtacttactac   180
IGHV1-66*01    cctggacagggacttgagtggattggatggatttatcctggaagtggtaatactaagtac   180
               ******** ** ***************   ***    *****  ** **  **** * **

VH2G8 patent   aatgagaagttcaagggcaaggccacattcactgcagatacatcctccaacacagcctac   231
IGHV1-9*01     aatgagaagttcaagggcaaggccacattcactgcagatacatcctccaacacagcctac   240
IGHV1-56*02    aatgagaaattcaagggcaaggccacactgactttagacacatcctccagcacagcctac   240
IGHV1-63*02    aatgagaagttcaagggcaaggccacactgactgcagacacatcctccagcacagcctac   240
IGHV1-63*01    aatgagaagttcaagggcaaggccacactgactgcagacaaatcctccagcacagcctac   240
IGHV1-54*02    aatgagaagttcaagggcaaggcaacactgactgcagacaaatcctccaacacagcctac   240
IGHV1-55*01    aatgagaagttcaagagcaaggccacactgactgtagacacatcctccagcacagcctac   240
IGHV1S61*01    aatgagaagttcaagagcaaggccacactgactgtagacacatcctccagcacagcctac   240
IGHV1-77*01    aatgagaagttcaagggcaaggccacactgactgcagacaaatcctccagcacagcctac   240
IGHV1-66*01    aatgagaagttcaagggcaaggccacactgacggcagacacatcctccagcactgcctac   240
               ******** ****** ******* *** * **   *** * ******** *** ******

VH2G8 patent   atgcaactcagcagcctgacatctgaggactctgccgtctattactgtgcaagagagggt   291
IGHV1-9*01     atgcaactcagcagcctgacaactgaggactctgccatctattactgtgcaaga------   294
IGHV1-56*02    atgcagctcagcagcctgacatctgaagactctgcggtctatttctgtgcaaga------   294
IGHV1-63*02    atgcagctcagcagcctgacatctgaggactctgccatctattactgtgcaaga------   294
IGHV1-63*01    atgcagttcagcagcctgacatctgaggactctgccatctattactgtgcaaga------   294
IGHV1-54*02    atgcagctcagcagcctgacatctgaggactctgcggtctatttctgtgcaaga------   294
IGHV1-55*01    atgcagctcagcagcctgacatctgaggactctgcggtctattactgtgcaaga------   294
IGHV1S61*01    atgcagctcagcagcctgacatctgacgactctgcggtctattattgtgcaaga------   294
IGHV1-77*01    atgcagctcagcagcctgacatctgaggactctgcagtctatttctgtgcaaga------   294
IGHV1-66*01    atgcagctcagcagcctaacatctgaggactctgcggtctattactgtgcaaga------   294
               *****  ********** *** **** ********  ******   *********

VH2G8 patent   tggtacttcgatgtctggggcgcagggaccacggtcaccgtctcctcagccaaaacaaca   351
IGHV1-9*01     ------------------------------------------------------------   294
IGHV1-56*02    ------------------------------------------------------------   294
IGHV1-63*02    ------------------------------------------------------------   294
IGHV1-63*01    ------------------------------------------------------------   294
IGHV1-54*02    ------------------------------------------------------------   294
IGHV1-55*01    ------------------------------------------------------------   294
IGHV1S61*01    ------------------------------------------------------------   294
IGHV1-77*01    ------------------------------------------------------------   294
IGHV1-66*01    ------------------------------------------------------------   294

VH2G8 patent   cccccatcagtctatccactggcc   375
IGHV1-9*01     ------------------------   294
IGHV1-56*02    ------------------------   294
IGHV1-63*02    ------------------------   294
IGHV1-63*01    ------------------------   294
IGHV1-54*02    ------------------------   294
IGHV1-55*01    ------------------------   294
IGHV1S61*01    ------------------------   294
IGHV1-77*01    ------------------------   294
IGHV1-66*01    ------------------------   294
```

Fig. 2 gccaaaacaacacccccatcagtctatccactggcc gccaaaacaacacccccatcagtctatccactggcccctgggtgtggaggtacaactggttcc
tccgtgactctgggatgcctggtcaagggctacttccctgagtcagtgactgtgacttggaactct
ggatccctgtccagcagtgtgcacaccttcccagctctcctgcagtctggactctacactatgag
cagctcagtgactgtcccctccagcacctggccaagtcagaccgtcacctgcagcgttgctca
cccagccagcagcaccacggtggacaaaaaacttgagcccagcgggcccatttcaacaat
caacccctgtcctccatgcaaggagtgtcacaaatgcccagctcctaacctcgagggtggac
catccgtcttcatcttccctccaaatatcaaggatgtactcatgatctccctgacacccaaggtca
cgtgtgtggtggtggatgtgagcgaggatgacccagacgtccagatcagctggtttgtgaaca
acgtggaagtacacacagctcagacacaaacccatagagaggattacaacagtactatccg
ggtggtcagcaccctccccatccagcaccaggactggatgagtggcaaggagttcaaatgc
aaggtcaacaacaaagacctcccatcacccatcgagagaaccatctcaaaaattaaaggg
ctagtcagagctccacaagtatacatcttgccgccaccagcagagcagttgtccaggaaaga
tgtcagtctcacttgcctggtcgtgggcttcaaccctggagacatcagtgtggagtggaccagc
aatgggcatacagaggagaactacaaggacaccgcaccagtcctggactctgacggttctta
cttcatatatagcaagctcaatatgaaaacaagcaagtgggagaaaacagattccttctcatg
caacgtgagacacgagggtctgaaaaattactacctgaagaagaccatctcccggtctccgg
gtaaa.

Fig. 3

```
                                                 <--------------------------------FR1-IMGT---------------------------------><----------
                                                   D  I  V  M  T  Q  S  P  L  T  L  S  V  T  I  G  Q  P  A  S  I  S  C  K  S  S  Q  S  L  L
                        Query_1        1   GATATCGTGATGACCCAGTCCCCACTCACTTTGTCGGTTACCATTGGACAACCAGCCTCTATCTCTTGCAAGTCAAGTCAGAGCCTCTTA  90
V  97.7% (292/299)  IGKV1-133*01   1   ...G.T............A.T.....................................................................  90
                                                   D  V  V  M  T  Q  T  P  L  T  L  S  V  T  I  G  Q  P  A  S  I  S  C  K  S  S  Q  S  L  L
V  94.3% (282/299)  IGKV1-135*01   1   ...G.T............A.T......................................C..............................  90
V  91.3% (273/299)  IGKV1-131*01   1   ...G.T............A.T......................................C..............................  90
V  90.6% (271/299)  IGKV1-132*01   1   ...G.T............A.T.....GT..............................................................  90
V  85.9% (244/284)  IGKV1-35*01    7   ------............A.T...........A..A.C.............T.......CG.........G............T......  90
V  79.6% (238/299)  IGKV1-110*02   1   ...G.T...........AA.T......T.CC..C.T..C.GTC.....G.T.A...T..C..........GA..T...........TG..  90
V  79.3% (237/299)  IGKV1-110*01   1   ...G.T...........AA.T......T.CC..C.T..C.GTC.....G.T.A......C..........GA..T...........TG..  90
V  79.9% (234/293)  IGKV1-122*01   7   ------...........AA.T......T.CC..C.T..C.GTC.....G.T.A......C..........G...T...........TGA.  90
V  78.9% (236/299)  IGKV1-117*02   1   ...G.T...........AA.T......T.CC..C.T..C.GTC.....G.T.A......C..........GA..T.........A.TG..  90
V  78.9% (236/299)  IGKV1-117*01   1   ...G.TT..........AA.T......T.CC..C.T..C.GTC.....G.T.A......C..........GA..T.........A.TG..  90

                                                 CDR1-IMGT----------><-------------------FR2-IMGT-------------------><CDR2-IM><--------
                                                   Y  S  N  G  N  T  H  L  N  W  L  L  Q  R  P  G  Q  S  P  K  R  L  I  Y  L  V  S  K  L  D
                        Query_1       91   TATAGTAATGGAAACACCCATTTGAATTGGTTATTACAGAGGCCAGGCCAGTCTCCAAAGCGCCTAATCTATCTGGTGTCTAAACTGGAC  180
V  97.7% (292/299)  IGKV1-133*01  91   ..............A...T.......................................................................  180
                                                   Y  S  N  G  K  T  Y  L  N  W  L  L  Q  R  P  G  Q  S  P  K  R  L  I  Y  L  V  S  K  L  D
V  94.3% (282/299)  IGKV1-135*01  91   G.....G.......G..AT.............G.........................................................  180
V  91.3% (273/299)  IGKV1-131*01  91   C.............G..AT..............CA.........T......G............T............A..C.........  180
V  90.6% (271/299)  IGKV1-132*01  91   ..............G..AT..............CA.........T......G.........A......G....A......C.........  180
V  85.9% (244/284)  IGKV1-35*01   91   C................AT.C...........TG....A..........CA......C...TT.....T...GG.....T.G....A..A  180
V  79.6% (238/299)  IGKV1-110*02  91   C.C..C............T....AT......ACC.G....A....................T...G.....CAG...T..C..C.GATTT  180
V  79.3% (237/299)  IGKV1-110*01  91   C.C...............T....AC......ACC.G....A....................T...G.....CAAA..T..C..C.GATTT  180
V  79.9% (234/293)  IGKV1-122*01  91   A.C...............T.......C....ACC.C....AA...............C...T...G.....CAG...T..C..C.GATTT  180
V  78.9% (236/299)  IGKV1-117*02  91   C.................T....AG.A....ACC.G....AA...................T...G.....CAAA..T..C..C.GATTG  180
V  78.9% (236/299)  IGKV1-117*01  91   C.................T....AG.A....ACC.G....AA...................T...G.....CAAA..T..C..C.GATTT  180

                                                 ---------------------------------------FR3-IMGT---------------------------------------
                                                   S  G  V  P  D  R  F  T  G  S  G  S  G  T  D  F  T  L  K  I  S  R  V  E  A  E  D  L  G  F
                        Query_1      181   TCTGGAGTCCCTGACAGGTTCACTGGCAGTGGATCAGGAACAGATTTTACACTGAAAATCAGCAGAGTGGAGGCTGAGGATTTGGGATTT  270
V  97.7% (292/299)  IGKV1-133*01  181   .......................................................................................G..  270
                                                   S  G  V  P  D  R  F  T  G  S  G  S  G  T  D  F  T  L  K  I  S  R  V  E  A  E  D  L  G  V
V  94.3% (282/299)  IGKV1-135*01  181   ......................................G........C.......................................G..  270
V  91.3% (273/299)  IGKV1-131*01  181   C....CA..........T....G..............AG......................................A.........G..  270
V  90.6% (271/299)  IGKV1-132*01  181   C....CA...............G..............A...............T.......................A.........G..  270
V  85.9% (244/284)  IGKV1-35*01   181   .....G..T.............G.........G..T...........C.....C..G..............................G..  270
V  79.6% (238/299)  IGKV1-110*02  181   .....G.....A..........G...............G........C.....C..G........................C.....G..  270
V  79.3% (237/299)  IGKV1-110*01  181   .....G.....A..........G...............G........C.....C..G........................C.....G..  270
V  79.9% (234/293)  IGKV1-122*01  181   .....G...TA...........G..T............G........C.......................................G..  270
V  78.9% (236/299)  IGKV1-117*02  181   .....G.....A..........G...............G.....Y..C.....C..G........................C.....G..  270
V  78.9% (236/299)  IGKV1-117*01  181   .....G.....A..........G...............G........C.....C..G........................C.....G..  270

                                                              --------><--------CDR3-IMGT--------><----------FR4-IMGT---------->
                                                               Y  Y  C  V  Q  G  T  H  F  P  Y  T  F  G  G  G  T  K  L  E  I  K
                                 Query_1      271   TATTACTGCGTGCAAGGTACACATTTTCCGTACACGTTCGGAGGGGGACCAAGCTGGAAATAAAAC  337
         V  97.7% (292/299)  IGKV1-133*01  271   .............................--------------------------------------  299
                                                                            Y  Y  C  V  Q  G  T  H  F  P
         V  94.3% (282/299)  IGKV1-135*01  271   .....T...TG..................--------------------------------------  299
         V  91.3% (273/299)  IGKV1-131*01  271   .........C...................--------------------------------------  299
         V  90.6% (271/299)  IGKV1-132*01  271   .........T...........T...A...--------------------------------------  299
         V  85.9% (244/284)  IGKV1-35*01   271   .........A......C...-----------------------------------------------  290
         V  79.6% (238/299)  IGKV1-110*02  271   ....T....T.T............G....--------------------------------------  299
         V  79.3% (237/299)  IGKV1-110*01  271   ....T....TCT...A........G....--------------------------------------  299
         V  79.9% (234/293)  IGKV1-122*01  271   ....T....C.C....T.......G.C..--------------------------------------  299
         V  78.9% (236/299)  IGKV1-117*02  271   .........T.T......T.....G....--------------------------------------  299
         V  78.9% (236/299)  IGKV1-117*01  271   .........T.T......T.....G....--------------------------------------  299
         J  100.0% (38/38)   IGKJ2*01        2   -----------------------------......................................  39
         J  92.1% (35/38)    IGKJ2*03        2   -----------------------------...T..........TC......................  39
         J  89.5% (34/38)    IGKJ2*02        2   -----------------------------...T..........TC.................G....  39
```

Fig. 4

Fig. 6A

```
VH2G8patent    ---------ctgcagcagtctggcgctgagctgatgaagcctggggcctcagtgaagata 51
VH2G8correct   caggtccagctgcagcagtctggcgctgagctgatgaagcctggggcctcagtgaagata 60
                        ***************************************************

VH2G8patent    tcctgcaaggctactggctacacactcagtagctactggctagagtgggtaaagcagagg 111
VH2G8correct   tcctgcaaggctactggctacacactcagtagctactggctagagtgggtaaagcagagg 120
               ************************************************************

VH2G8patent    cctggacatggccttgagtggattggagagatttacctggaagtggtagtactaactac 171
VH2G8correct   cctggacatggccttgagtggattggagagatttacctggaagtggtagtactaactac 180
               ************************************************************

VH2G8patent    aatgagaagttcaagggcaaggccacattcactgcagatacatcctccaacacagcctac 231
VH2G8correct   aatgagaagttcaagggcaaggccacattcactgcagatacatcctccaacacagcctac 240
               ************************************************************

VH2G8patent    atgcaactcagcagcctgacatctgaggactctgccgtctattactgtgcaagagagggt 291
VH2G8correct   atgcaactcagcagcctgacatctgaggactctgccgtctattactgtgcaagagagggt 300
               ************************************************************

VH2G8patent    tggtacttcgatgtctggggcgcagggaccacggtcaccgtctcctcagccaaaacaaca 351
VH2G8correct   tggtacttcgatgtctggggcgcagggaccacggtcaccgtctcctca------------ 348
               ************************************************

VH2G8patent    cccccatcagtctatccactggcc 375
VH2G8correct   ------------------------ 348
```

Fig. 6B

```
VH2G8PATENT    ---LQQSGAELMKPGASVKISCKATGYTLSSYWLEWVKQRPGHGLEWIGEILPGSGSTNY
VH2G8CORRECT   QVQLQQSGAELMKPGASVKISCKATGYTLSSYWLEWVKQRPGHGLEWIGEILPGSGSTNY
                  *********************************************************

VH2G8PATENT    NEKFKGKATFTADTSSNTAYMQLSSLTSEDSAVYYCAREGWYFDVWGAGTTVTVSSAKTT
VH2G8CORRECT   NEKFKGKATFTADTSSNTAYMQLSSLTSEDSAVYYCAREGWYFDVWGAGTTVTVSS----
               ********************************************************

VH2G8PATENT    PPSVYPLA
VH2G8CORRECT   --------
```

```
VH
1) 3HC4, 2) 4KQ3, 3) 5HHW
A) Humanized VH coming from the single framework analysis
B) Resulting humanized VH

1 QVQLVQSGAEVKKPGESVKVSCKASGYTFTTYYLNWVRQAPGQGLEWMGRIYPGNGHAQYNEKFKGRVTITADKSTSTAYMELSSLRSEDTAVYYCARSWEGFDY-WGQGTTVTVSS
2 QVQLVQSGAEVKKPGSSVKVSCKASGGTFSSYAISWVRQAPGQGLEWMGSIIPWFGTTNYAQKFQGRVTITADESTSTAYMELSSLRSEDTAVYYCARDSEYYFDHWGQGTLVTVSS
3 QVQLVQSGAEVKKPGASVKVSCKASGYTFTSYYMHWVRQAPGQGLEWMGIINPSGGSTSYAQKFQGRVTMTRDTSISTAYMELSRLRSDDTAVYYCARGGWFDY---WGQGTLVTVSS
A QVQLVQSGAEVKKPGASVKVSCKASGYTLSSYWLHWVQQSPGQGLEWMGEILPGSGSTNYAQKFQGRVTITADKSTSTAYMELSSLRSEDTAVYYCAREGWYFDV-WGAGTTVTVSS
B QVQLVQSGAEVKKPGASVKVSCKASGYTLSSYWIHWVRQAPGQGLEWMGWILPGSGSTNYAQKFQGRVTITADKSTSTAYMELSSLRSEDTAVYYCAREGWYFDV-WGQGTLVTVSS
                                                                      * •                **
*: amino acids back mutated to the murine sequence (M48I, R67K, V68A)
•: amino acid was chosen because belonging to the sequence with the best homology score and the lowest X-ray crystallographic resolution.


VL
1) 4DTG, 2) 4LKX, 3) 4LRI
C) Humanized VL coming from the single framework analysis
D) Resulting humanized VH

1 DIVMTQTPLSLSVTPGQPASISCKSSQSLLDSDGKTYLNWYLQKPGQSPQLLIYLVSKLDSGVPDRFSGSGSGTDFTLKISRVEAEDVGVYYCLQATHFPQTFGGGTKVEIK
2 DIVMTQTPLSLSVTPGQPASISCRSSQSIVHSNGNTYLEWYLQKPGQSPQLLIYKVSNRFSGVPDRFSGSGSGTDFTLKISRVEAEDVGVYYCFQGSHVPFTFGGGTKVEIK
3 DIVMTQSPLSLSVTPGEPASISCRSSQSLLHTNGYNYLDWYVQKPGQSPQLLIYLASNRASGVPDRFSGSGSGTDFTLKISRVETEDVGVYYCMQALQIPRTFGQGTKVEIK
C DIVMTQTPLSLSVTPGQPASISCKSSQSLLYSNGNTHLNWFQQRPGQSPRRLIYLVSNRASGVPDRFSGSGSGTDFTLKISRVEAEDVGVYYCVQGTHFPYTFGGGTKLEIK
D DIVMTQTPLSLSVTPGQPASISCRSSQSLLYSNGNTHLNWYLQKPGQSPQLLIYLVSNRASGVPDRFSGSGSGTDFTLKISRVEAEDVGVYYCVQGTHFPYTFGGGTKVEIK
                        *                   *                  *
```

Fig. 8

<Peak Table>

UV 280nm

| Peak# | Ret. Time | Area | Area% |
|---|---|---|---|
| 1 | 7.635 | 9750 | 0.462 |
| 2 | 8.710 | 111335 | 5.276 |
| 3 | 10.223 | 1989121 | 94.262 |
| Total | | 2110214 | 100.000 |

HUMANISED ANTIBODIES AGAINST PATHOGENIC FUNGI

CROSS-REFERENCE TO RELATED APPLICATIONS

This application is the U.S. national phase of International Application No. PCT/EP2021/080372 filed Nov. 2, 2021, which designated the U.S. and claims priority to IT Patent Application No. 102020000026398 filed Nov. 5, 2020, the entire contents of each of which are hereby incorporated by reference.

REFERENCE TO SEQUENCE LISTING SUBMITTED ELECTRONICALLY

The contents of the electronically submitted sequence listing (Name: 2149_0308_Sequence_Listing_ST25.txt, Size: 65,255 bytes, and Date of Creation: Apr. 10, 2026, is herein incorporated by reference in its entirety.

STATE OF THE ART

Fungal infections cause life-threatening diseases such as fungaemia, pneumonia, chronic pulmonary aspergillosis, bronchopulmonary aspergillosis and cryptococcosis (David S P et al., Lancet Infect Dis 2017; 17: e383-92; Darius A J et al., Lancet Infect Dis 2017; 17: e393-402). These pathologies affect mainly patients undergoing organ transplantation, surgery and neoplastic disease, immunocompromised subjects and premature infants. About 3,000,000 cases of chronic pulmonary aspergillosis, 223,100 cases of cryptococcal meningitis complicating HIV/AIDs, 700,000 cases of invasive candidiasis, 500,000 cases of *Pneumocystis jirovecii* pneumonia, 250,000 cases of invasive aspergillosis, 100,000 cases of disseminated histoplasmosis, over 10,000,000 cases of fungal asthma are reported annually (Bongomin F et al., J. Fungi 2017; 3:57). Of the five million fungal species (spp.) existent, only 300 are considered dangerous for humans, and ~10% of them are recurrent. The most common fungi isolated in invasive diseases are *Candida* spp., *Cryptococcus* spp., and *Aspergillus* spp. The mortality rate for invasive candidiasis is about 40%, from 20 to 30% for cryptococcosis and 20% for aspergillosis. These data are referred to wealthy countries with a fully functional healthcare system, while where resources are limited the death rate surpasses 50% (Nyazika T K et al., J. Med. Microbiol. 2016; 65:1281-1288). Candidiasis is the second most frequent fungal infection. Despite *C. albicans* is the most prevalent specie, there have been an increasing number of infections caused by non-albicans *Candida* spp. (NACs). This shift towards NACs appears to be due to the massive use of antifungal drugs leading to the selection of species with an innate resistance or higher tolerance. Together, *C. albicans, C. krusei, C. parapsilosis* and *C. tropicalis* represent the 80% of the total cases of infections and 49.5% of them are caused by NACs.

The discovery of new frightening fungal species makes the run for drugs more urgent. This is the case of *C. auris* which appeared for the first time in 2009 (Satoh K et al. Microbiol Immunol. 2009; 53:41-4) and spread rapidly all over the world. It commonly presents multidrug resistance to every class of antifungal drugs. The MIC of different strains for fluconazole range from 32 to ≥64 mg/L while for voriconazole the MIC is about 16 mg/L. 30% of the strains have a low susceptibility to Amphotericin B (MIC≥2 mg/L) and recent studies have confirmed an increasing resistance to echinocandins (MIC≥8 mg/L). *C. auris* is tolerant to high salt concentrations, where it tends to assume a rudimental pseudohyphal form, and to high temperatures (42° C.). *C. auris* can adhere to biotic and abiotic surfaces and colonize them for weeks and months becoming a serious problem for the invasive devices used in the hospitals.

Until now, the leading classes of antifungals are: polyenes, pyrimidine analogues, azoles and echinocandins.

Toxicity represents the main issue of current and new antifungal agents. The action spectrum of antifungal agents should be balanced, not too limited but also not too broad: effective against several species but not subject to early resistance. They should be stable and have limited off-target interactions and a known pharmacokinetic. The way of administration may be chosen preferring the patient compliance and considering hypothetical comorbidities.

Despite several antifungal entities and new targets under investigation (Gintjee T J et al. J. Fungi 2020; 6:28; Perfect J R Nat Rev Drug Discov. 2017; 16:603-616), none of them has entered the market yet.

Among the novel therapeutic strategies to treat fungal diseases, the employment of monoclonal antibodies seems to be a great step forward.

The antifungal sector attended the birth of several monoclonal antibodies (Di Mambro T et al. Front Pharmacol. 2019; 10:80). Matthews R C et al. in Antimicrob Agents Chemother. 2003; 47: 2208-2216 describe Mycograb, a recombinant antibody directed against fungal Hsp90, a member of the Heat Shock Proteins family. Mycograb consists of the antigen-binding variable domains of antibody heavy and light chains linked together to create a recombinant protein which is expressed in *Escherichia coli*. It does not have a Fc component. Benefits were not considered to outweigh the risks (EMEA/129723/2007) and the product did not entered the clinic.

mAb 2G8 has been described as a successful murine mAb able to specifically recognize β-1,3 glucans of pathogenic fungi. mAb 2G8 showed in vitro activity against *Candida* spp. and *Aspergillus* spp. It showed a strongly efficacy in vivo in a systemic mouse model of *Candida* infection and in a rat model of vaginal candidiasis (Torosantucci A et al. J Exp Med. 2005; 202: 597-606). The activity was verified also on *Cryptococcus neoformans*, confirming the capability to bind and inhibit the growth and capsule formation of this fungal species in vitro and in vivo (Rachini A et al. Infection and Immunity 2007; 75:5085-94). WO2006030318 describes 2G8 VH sequence (SEQ ID NO: 2) and VL sequence (SEQ ID NO: 1).

```
(2G8 Light chain variable region)
                                        SEQ ID NO: 1
DIVMTQSPLTLSVTIGQPASISCKSSQSLLYSNGNTHLNW

LLQRPGQSPKRLIYLVSKLDSGVPDRFTGSGSGTDFTLKI

SRVEAEDLGFYYCVQGTHEPYTFGGGTKLEIKRADAAPTV

S

(2G8 Heavy chain variable region)
                                        SEQ ID NO: 2
LQQSGAELMKPGASVKISCKATGYTLSSYWLEWVKQRPGH

GLEWIGEILPGSGSTNYNEKFKGKATFTADTSSNTAYMQL

SSLTSEDSAVYYCAREGWYFDVWGAGTTVTVSSAKTTPPS

VYPLA
```

However, the murine source of this antibody precludes the possibility to use it in humans. At present, several attempts to obtain a humanised antibody from mAb 2G8, by using the state of the art technologies, failed.

Therefore, there is a strong need for novel, safe and efficient monoclonal antibodies based antifungal treatment.

DESCRIPTION

It forms a first object of the present invention humanised monoclonal antibodies, or fragments or fusions proteins thereof, that recognize and bind β-1,3 glucans, favouring the human innate immunity against pathogenic fungi. In a second aspect, it is here described and claimed a combination of a) at least one humanised antibody that recognize and bind β-1,3 glucans and b) at least one antifungal agent, preferably an echinocandin and/or polyene macrolide.

DESCRIPTION OF THE FIGURES

FIG. 1: Comparison of the 10 germlines amino acidic sequences and SEQ ID NO: 2, (2G8 Heavy chain variable region according to WO2006030318). Sequences shown are as follows: Query_1 AA: SEQ ID NO: 31, Query_1 DNA: SEQ ID NO: 29, IGHV1-9*01: SEQ ID NO: 30, IGHV1-9*01 AA: SEQ ID NO: 44, IGHV1-63*01: SEQ ID NO: 32, IGHV1-55*01: SEQ ID NO: 33, IGHV1-56*01: SEQ ID NO: 34, IGHV1-77*01: SEQ ID NO: 35, IGHV1-63*02: SEQ ID NO: 36, IGHV1-54*02: SEQ ID NO: 37, IGHV1-56*02: SEQ ID NO: 38, IGHV1S61*01: SEQ ID NO: 39, IGHV1-66*01: SEQ ID NO: 40, IGHJ1*01: SEQ ID NO: 41, IGHJ1*02: SEQ ID NO: 42, and IGHJ1*03: SEQ ID NO: 43.

FIG. 2: Comparison of the 10 germline nucleotide sequences and SEQ ID NO: 6, (VH2G8patent: Heavy chain variable region according to WO2006030318). The 10 germline nucleotide sequences shown are as follows: IGHV1-9*01: SEQ ID NO: 45, IGHV1-56*02: SEQ ID NO: 46, IGHV1-63*02: SEQ ID NO: 47, IGHV1-63*01: SEQ ID NO: 48, IGHV1-54*02: SEQ ID NO: 49, IGHV1-55*01: SEQ ID NO: 50, IGHV1S61*01: SEQ ID NO: 51, IGHV1-77*01: SEQ ID NO: 52, and IGHV1-66*01: SEQ ID NO: 53.

FIG. 3: Comparison between the C terminal portion, i.e., residues 350-375, of SEQ ID NO: 6 (grey) and the constant regions IGHV accession number IMGT EF392837 (SEQ ID NO: 54).

FIG. 4: Comparison of the 10 germline nucleotide sequences and SEQ ID NO: 1, (2G8 Light chain variable region according to WO2006030318). Sequences shown are as follows: Query_1 AA: SEQ ID NO: 57, Query_1 DNA: SEQ ID NO: 55, IGKV1-133*01: SEQ ID NO: 56, IGKV1-133*01 AA: SEQ ID NO: 70, IGKV1-135*01: SEQ ID NO: 58, IGKV1-131*01: SEQ ID NO: 59, IGKV1-132*01: SEQ ID NO: 60, IGKV1-35*01: SEQ ID NO: 61, IGKV1-110*02: SEQ ID NO: 62, IGKV1-110*01: SEQ ID NO: 63, IGKV1-122*01: SEQ ID NO: 64, IGKV1-117*02: SEQ ID NO: 65, IGKV1-117*01: SEQ ID NO: 66, IGKJ2*01: SEQ ID NO: 67, IGKJ2*03: SEQ ID NO: 68, and IGKJ2*03: SEQ ID NO: 69.

FIG. 6: Comparison between the described murine 2G8 VH sequence and the here identified 2G8 $VH_c$ sequence, (A) nucleotide SEQ ID NO: 6 (VH2G8patent) versus SEQ ID NO: 8 (VH2G8correct); (B) amino acids, SEQ ID NO: 2 (VH2G8PATENT) versus SEQ ID NO: 4 (VH2G8CORRECT).

FIG. 8: Humanisation of the 2G8 antibody, second approach. Comparison of 2G8 H2 sequence (SEQ ID NO: 18) and 2G8 K2 sequence (SEQ ID NO: 17) with sequences identified as most similar in PDB. Sequences shown are as follows: 3HC4: SEQ ID NO: 92, 4KQ3: SEQ ID NO: 93, 5NHW: SEQ ID NO: 94, VH A: SEQ: ID NO: 18, VH B: SEQ ID NO: 95, 4DTG: SEQ ID NO: 96, 4LKX: SEQ ID NO: 97, 4LRI: SEQ ID NO: 98, VL C: SEQ ID NO: 18, and VL D: SEQ ID NO: 99.

Figure 5A:
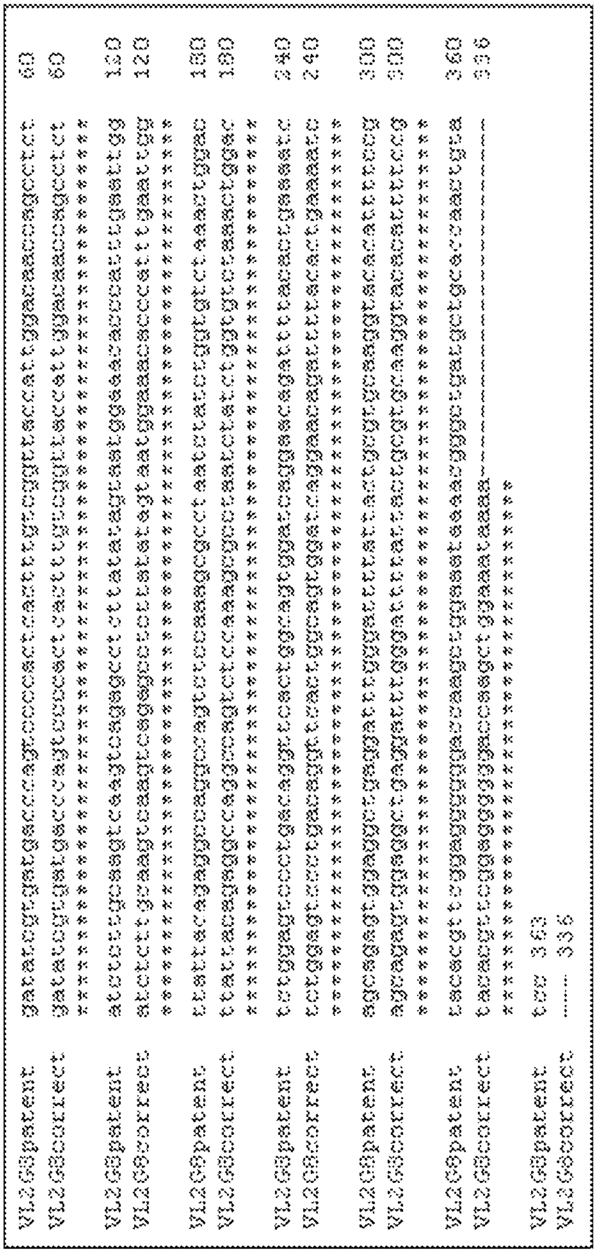
FIG. 5: Comparison between the described murine 2G8 VL sequence and the here identified 2G8 $VL_c$ sequence: (A) nucleotide SEQ ID NO: 5 (VL2G8patent) versus SEQ ID NO: 7 (VL2G8correct); (B) amino acids, SEQ ID NO: 1 (VL2G8PATENT); versus SEQ ID NO: 3 (VL2G8CORRECT).
Figure 5B:
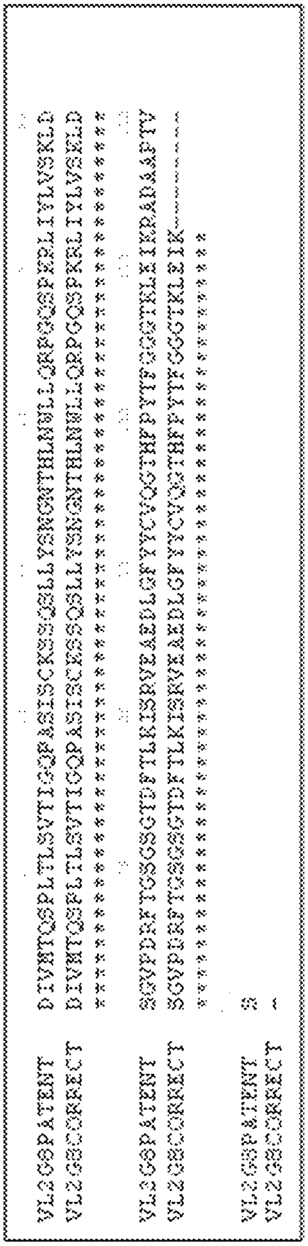

Sequence Listings: SEQ ID NO: 1-28 are provided.

DETAILED DESCRIPTION OF THE INVENTION

The residues in antibody variable domains are conventionally numbered according to a system devised by Kabat, see Johnson G and Te Wua T, Nucleic Acids Res. 2000; 28: 214-218 for a review. This numbering system is used in the present specification except where otherwise indicated.

The term "variable region" or "variable domain" refers to the domain of an antibody heavy or light chain that is involved in binding the antibody to antigen.

The variable domains of the heavy chain and light chain (VH and VL, respectively) of a native antibody generally have similar structures, with each domain comprising four conserved Framework regions (FRs) and three Complementarity-determining regions (CDRs).

As used herein, the term 'humanised antibody' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotech. 1998; 16: 535-539. In one embodiment, rather than the entire CDR being transferred, only one or more of the specificity determining residues from any one of the CDRs described herein are transferred to the human antibody framework. In one embodiment, only the specificity determining residues from one or more of the CDRs described herein are transferred to the human antibody framework. In another embodiment, only the specificity determining residues from each of the CDRs described herein are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions.

Thus, provided in one embodiment is a humanised antibody which binds β-1,3 glucans, wherein the variable domain comprises human acceptor framework regions and non-human donor CDRs.

A murine anti β-1,3 glucans antibody, referred to herein as mAb 2G8, was described in WO2006030318 and the amino acidic sequences of the variable regions of this antibody are provided in FIG. 1 and in FIG. 4 (SEQ ID NO: 2, SEQ ID NO: 1), respectively.

The CDRs sequences characterising the humanised antibodies according to the present invention have been surprisingly identified by the Applicant.

In an attempt to obtain a humanised version of the mAb 2G8, the authors of the present invention generated and then randomly combined several heavy and light chains and screened the resulting recombinant mAbs. Unexpectedly, only constructs comprising the CDRs listed below were biologically active and with an affinity for β-1,3 glucans higher than the affinity observed for murine 2G8.

Several hmAb 2G8 characterized by comprising the listed CDRs were produced and characterized and demonstrated capable to recognize a number of fungi.

In a first embodiment, here it is described and claimed a humanised antibody, or fragments or fusion proteins thereof, comprising an antigen-binding region that is specific for recognizing β-1,3 glucans, comprising:

(i) a CDRH1 having at least 90% of identity with the sequence SYWLE (SEQ ID NO: 10)

(ii) a CDRH2 having at least 90% of identity with the sequence EILPGSGSTNYNEKFKG (SEQ ID NO: 12)

(iii) a CDRH3 having at least 90% of identity with the sequence EGWYFDV (SEQ ID NO: 14)

(iv) a CDRL1 having at least 90% of identity with the sequence QSLLYSNGNTH (SEQ ID NO: 9)

(v) a CDRL2 having at least 90% of identity with the sequence LVS (SEQ ID NO: 11), and (vi) a CDRL3 having at least 90% of identity with the sequence VQGTHFPYT (SEQ ID NO: 13).

In an embodiment, said humanised antibody, or fragments or fusion proteins thereof, comprises variable regions having CDR sequences of:

(i) CDRH1 comprising sequence SYWLE (SEQ ID NO: 10)

(ii) CDRH2 comprising sequence EILPGSGSTNYNEKFKG (SEQ ID NO: 12)

(iii) CDRH3 comprising sequence EGWYFDV (SEQ ID NO: 14)

(iv) CDRL1 comprising sequence QSLLYSNGNTH (SEQ ID NO: 9)

(v) CDRL2 comprising sequence LVS (SEQ ID NO: 11), and (vi) CDRL3 comprising sequence VQGTHFPYT (SEQ ID NO: 13).

Antibodies or fragments thereof may be polyclonal or monoclonal antibodies. Monoclonal antibodies are preferred.

The antibodies include antibody-conjugates and molecules comprising the antibodies, such as chimeric molecules; chimeric receptors comprising one or more stimulatory, signalling, and/or costimulatory domains; and chimeric antigen receptors (CARs). Thus, an antibody includes, but is not limited to, full-length and native antibodies, as well as fragments and portions thereof retaining the binding specificities thereof, such as any specific binding portion thereof, including those having any number of, immunoglobulin classes and/or isotypes (e.g., IgG1, IgG2, IgG3, IgG4, IgM, IgA, IgD, IgE and IgM); and biologically relevant (antigen-binding) fragments or specific binding portions thereof, including but not limited to Fab, F(ab')2, Fv, and scFv (single chain or related entity).

In some embodiments, the antibody is a full-length IgG class antibody.

In some embodiments, said antibody fragments are Antigen-binding fragment (Fab). In some embodiments, said fusion proteins are single-chain variable fragment (scFv), or multimeric formats such as multivalent scFvs (diabody, triabody, and tetrabody).

In an embodiment, an antibody of the present disclosure, or fragments or fusion proteins thereof, comprises a heavy chain, wherein the variable domain of the heavy chain comprises a sequence having at least 60% identity or similarity to the sequence H5 given in SEQ ID NO:22.

In one embodiment, an antibody of the present disclosure comprises a heavy chain, wherein the variable domain of the heavy chain comprises a sequence having at least 70%, 80%, 90%, 95% or 98% identity or similarity to the sequence to the sequence H5 given in SEQ ID NO: 22.

"Identity", as used herein, indicates that at any particular position in the aligned sequences, the amino acid residue is identical between the sequences.

"Similarity", as used herein, indicates that, at any particular position in the aligned sequences, the amino acid residue is of a similar type between the sequences. For example, leucine may be substituted for isoleucine or valine.

Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);
asparagine and glutamine (amino acids having amide side chains); and
cysteine and methionine (amino acids having sulphur-containing side chains).

Degrees of identity and similarity can be readily calculated (Computational Molecular Biology, Lesk A M, ed., Oxford University Press, New York, 1988).

In another embodiment, an antibody of the present disclosure comprises a light chain, wherein the variable domain of the light chain comprises a sequence having at least 60% identity or similarity to the sequence K1 given in SEQ ID NO: 15.

In one embodiment the antibody of the present disclosure comprises a light chain, wherein the variable domain of the light chain comprises a sequence having at least 70%, 80%, 90%, 95% or 98% identity or similarity to the sequence K1 given in SEQ ID NO: 15.

In another embodiment of the disclosure, the antibody comprises a heavy chain and a light chain, wherein the variable domain of the heavy chain comprises a sequence having at least 60% identity or similarity to the sequence given in SEQ ID NO: 22 and the variable domain of the light chain comprises a sequence having at least 60% identity or similarity to the sequence given in SEQ ID NO: 15.

Suitably, the antibody comprises a heavy chain, wherein the variable domain of the heavy chain comprises a sequence having at least 70%, 80%, 90%, 95% or 98% identity or similarity to the sequence given in SEQ ID NO: 22 and a light chain, wherein the variable domain of the light chain comprises a sequence having at least 70%, 80%, 90%, 95% or 98% identity or similarity to the sequence given in SEQ ID NO: 15.

In an embodiment, the antibody comprises variable region sequences consisting of H5, SEQ ID NO: 22 for the heavy chain variable regions in combination with sequences consisting of K1, SEQ ID NO: 15 for the light chain variable regions.

In an embodiment, the humanised antibody is hmAb H5/K1.

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof. DNA sequences which encode an antibody molecule of the present invention can be obtained by methods well known to those skilled in the art.

The present invention also relates to a cloning or expression vector comprising one or more DNA sequences of the present invention. Accordingly, provided is a cloning or expression vector comprising one or more DNA sequences encoding an antibody of the present invention. Suitably, the cloning or expression vector comprises two DNA sequences, encoding the light chain and the heavy chain of the antibody molecule of the present invention, respectively and suitable signal sequences.

The present invention also relates to a host cell comprising one or more cloning or expression vectors comprising one or more DNA sequences encoding an antibody of the present invention. Any suitable host cell/vector system may be used for expression of the DNA sequences encoding the antibody molecule of the present invention.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

As the antibodies of the present invention are useful in the treatment of fungal infections, the present invention also provides a pharmaceutical composition comprising an antibody molecule of the present invention in combination with one or more of a pharmaceutically acceptable excipient, diluent or carrier.

In a further aspect, it is here claimed a humanised antibody according to the present invention or a pharmaceutical composition comprising the same for use in the treatment or prophylaxis of infections of human cells.

In a preferred embodiment, said infections are mediated by pathogenic fungi, preferably selected in the group comprising the genus *Candida, Aspergillus, Cryptococcus.*

In a further embodiment, the Applicant has surprisingly found that antibodies with a specificity for β-1,3 glucans can be successfully used in association with antifungal agents.

In particular, the Applicant has now surprisingly found that the combination of antibodies with a specificity for β-1,3 glucans with at least one antifungal agents, preferably selected from echinocandins or polyene macrolide, has a synergistic effect in inhibiting the growth of fungi.

In the present description, the expression "synergistic effect" means that the combination of humanised antibodies with a specificity for β-1,3 glucans with at least one antifungal agents, preferably selected from echinocandins or polyene macrolide, inhibits the growth of fungi at a concentration lower than the sum of the concentrations of humanised antibodies with a specificity for β-1,3 glucans and of the antifungal agent used alone for the same strain to obtain the same inhibition. In other words, a synergistic effect means that the combination of humanised antibodies with a specificity for β-1,3 glucans and of the antifungal agent is effective in producing more than the additive effect of each component in the same strain.

Therefore, it is here claimed a combination of a) at least one humanised antibody which has specificity for β-1,3 glucans and b) one or more antifungal agents for use in the treatment or prophylaxis of infections of human cells.

Said combination is for simultaneous, separate or sequential use as a medicament.

In an embodiment, this combination can be a simple combination of pharmaceutical forms of the individual active ingredients, the dosage of which will be established according to modalities deriving from the application of the teachings of the present invention, that is to say, reduced doses such as to ensure the reciprocal synergism and, if so desired, the reduction or disappearance of side effects. In this case, the combination according to the present invention can also be in the form of a kit, i.e. a pack containing the individual dosage forms of the active ingredients and the instructions for their simultaneous, separate or sequential administration. Alternatively, the present invention provides for a new pharmaceutical composition containing the at least two active ingredients in a single dosage form.

In a preferred aspect, said antifungal agent is selected from echinocandins and/or polyene macrolide.

Preferably, said echinocandin is caspofungin, micafungin, or anidulafungin.

Preferably, said polyene macrolide is amphotericin B.

In an embodiment, said composition comprises a hmAb according to the present invention in combination with a further antifungal agent.

In an embodiment, said humanised antibody is hmAb 2G8 H5/K1.

In a further embodiment, it is here claimed a method of treatment or prophylaxis of fungal infections in a human comprising administering to a human in need thereof a therapeutically effective amount of a) at least one humanised antibody which has specificity for β-1,3 glucans and b) one or more antifungal agents, preferably selected from echinocandins or polyene macrolide.

In a preferred embodiment, said fungal infections are selected from candidiasis, aspergillosis, cryptococcosis, dermatomycoses, sporotrichosis and other subcutaneous mycoses.

Humanised antibodies according to the present invention are capable of inhibiting the binding of a microbial pathogen that contains β-1,3 glucans in the cell wall to a human cell, therefore blocking or limiting infection of human cells.

Antibodies of the invention preferably bind a microbial pathogen that contains β-1,3 glucans in the cell wall and promote the recognition and phagocytosis of said complex by human macrophages favouring the human innate immunity against pathogenic fungi.

The present invention is further described by way of illustration only in the following examples.

EXAMPLE

Example 1: Definition of the Murine 2G8 $VH_c$ and $VL_c$ Sequences

The previously described mAb 2G8 VH amino acidic sequence (SEQ ID NO: 2) and 2G8 VL amino acidic sequence (SEQ ID NO: 1) have been analysed using IgBlast-Tool (ncbi.nlm.nih.gov/igblast/) murine databases IMGT mouse V genes, IMGT mouse D genes, IMGT mouse J genes.

The mAb 2G8 VH amino acidic sequence, SEQ ID NO: 2, has been analysed against the first 10 homologous germline sequences, i.e.

IGHV1-9*01 (accession number AC090843),
IGHV1-63*02 (accession number D14633),
IGHV1-55*01 (accession number AC074329),
IGHV1-56*01 (accession number AC087166),
IGHV1-77*01 (accession number AC160473),
IGHV1-54*02 (accession number X02064),
IGHV1-56*02 (accession number AF304551),
IGHV1S61*01 (accession number D14634),
IGHV1-66*01 (accession number AC073939).

The results of the comparison, reported in FIG. 1, highlighted an homology higher than 88.4%.

The nucleotide sequences of the first 10 homologous germline sequences identified above have been then compared with the nucleotide sequence of the prior art mAb 2G8 VH nucleotide sequence (SEQ ID NO: 6).

In the prior art mAb 2G8 VH sequence (SEQ ID NO: 6), the nucleotides codifying the 3 amino acids at the N terminus have been identified as lacking.

The comparisons are reported in FIG. 2, highlighted in grey the lacking nucleotides.

Moreover, the comparison showed that the first domain of the heavy chain constant region, highlighted in the sequence reported in FIG. 3, is not to be considered part of FR4 as can be seen from a comparison of this sequence with the constant region of another murine antibody i.e. IGHV accession number IMGT EF392837, detailed in the same FIG. 3.

From the above reported observations, the authors defined the 2G8 $VH_c$ sequence (SEQ ID NO: 8), containing 3 additional amino acids at the N terminus and stopping at amino acid Serin 116.

A similar approach was used to identify the sequence 2G8 $VL_c$. The germline sequences with higher homology show a percentage that was over 78.9%. In FIG. 4 is reported the comparison versus the first 10 homologous germline sequences listed below:

IGKV1-133*01 (accession number Z72382),
IGKV1-135*01 (accession number Z72384),
IGKV1-131*01 (accession number AJ231197),
IGKV1-132*01 (accession number AJ231198),
IGKV1-35*01 (accession number AJ231200),
IGKV1-110*02 (accession number M28132),
IGKV1-110*01 (accession number D00080),
IGKV1-122*01 (accession number D00082),
IGKV1-117*02 (accession number M28134),
IGKV1-117*01 (accession number D00081).

The authors defined a 2G8 $VL_c$ sequence (SEQ ID NO: 3), stopping at amino acid Lysin 112.

The newly defined amino-acidic and nucleotidic sequences, 2G8 $VL_c$(SEQ ID NO: 7, SEQ ID NO: 3, respectively) and 2G8 $VH_c$(SEQ ID NO: 4, SEQ ID NO: 8, respectively) are reported in FIG. 5A, FIG. 5B and FIG. 6A, FIG. 6B, respectively, in comparison to the sequences described in WO2006030318.

Example 2: Obtainment of Humanised Antibodies

Example 2A, First Approach

Figure 7A:
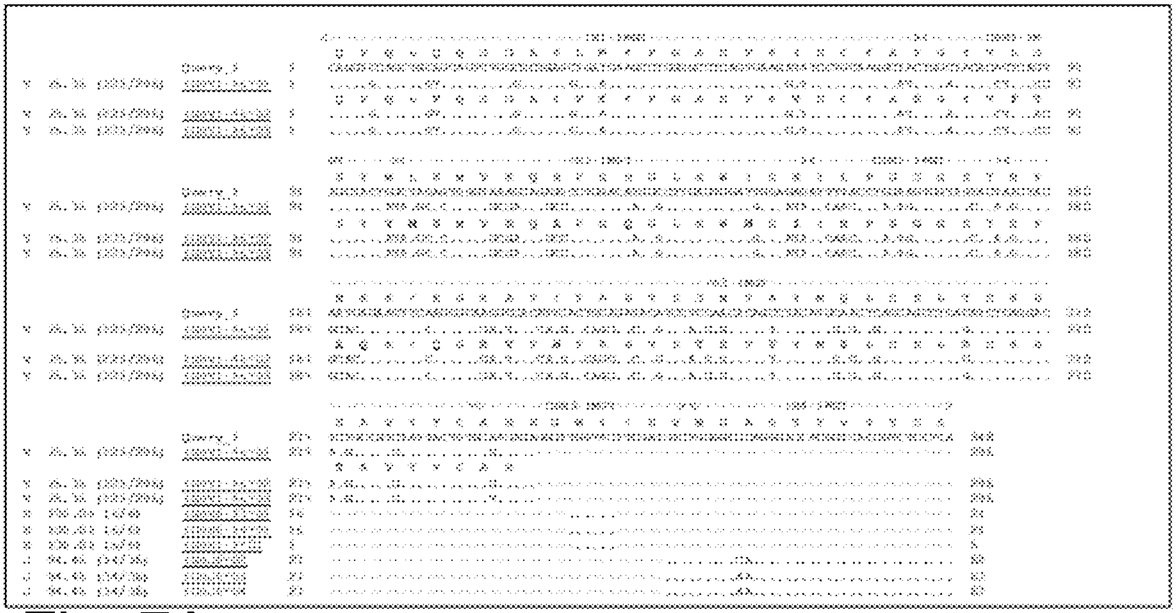
FIG. 7: Humanisation of the 2G8 antibody, first approach. (A) Comparison between the 2G8 $VH_c$ sequence (SEQ ID NO: 4) with the most homologous human germline IGHV1-46*01. Sequences shown are as follows: Query_1 AA: SEQ ID NO: 71, Query_1 DNA: SEQ ID NO: 72, IGHV1-46*01: SEQ ID NO: 73, IGHV1-46*01 AA: SEQ ID NO: 74, IGHV1-46*02: SEQ ID NO: 75, IGHV1-46*03: SEQ ID NO: 76, IGHD6-13*01: SEQ ID NO: 77, IGHD6-19*01: SEQ ID NO: 78, IGHD1-1*01: SEQ ID NO: 79, IGHJ6*02: SEQ ID NO: 80, IGHJ6*03: SEQ ID NO: 81, and IGHJ6*04: SEQ ID NO: 82; (B) amino-acids comparison between the 2G8 $VH_c$ sequence (SEQ ID NO: 4, VH2G8MURINE) and H1 2G8 (SEQ ID NO: 16, VH2G8HUMANISED); (C) Comparison of the 2G8 $VL_c$ sequence (SEQ ID NO: 3) with the most homologous human germline IGKV2-30*01. Sequences shown are as follows: Query_1 AA: SEQ ID NO: 83, Query_1 DNA: SEQ ID NO: 84, IGKV2-30*01: SEQ ID NO: 85, IGKV2-30*01 AA: SEQ ID NO: 86, IGKV2-30*02: SEQ ID NO: 87, IGKV2D-30*01: SEQ ID NO: 88, IGKJ4*02: SEQ ID NO: 89, IGKJ4*01: SEQ ID NO: 90, and IGKJ2*01: SEQ ID NO: 91.
Figure 7B:
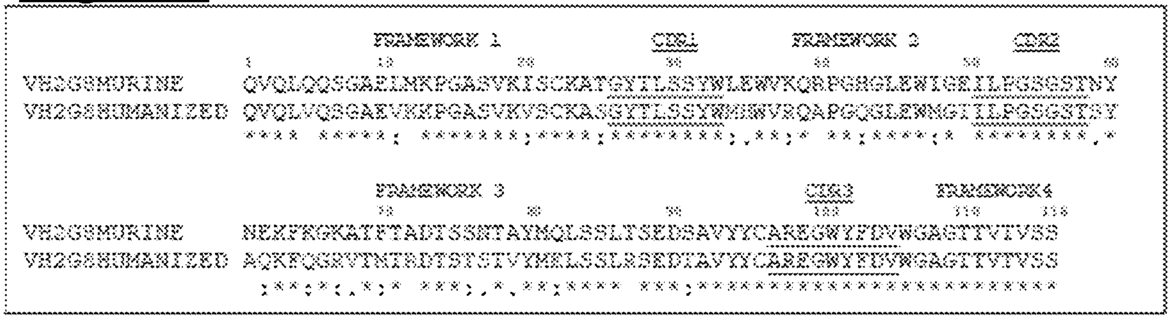
Figure 7C:
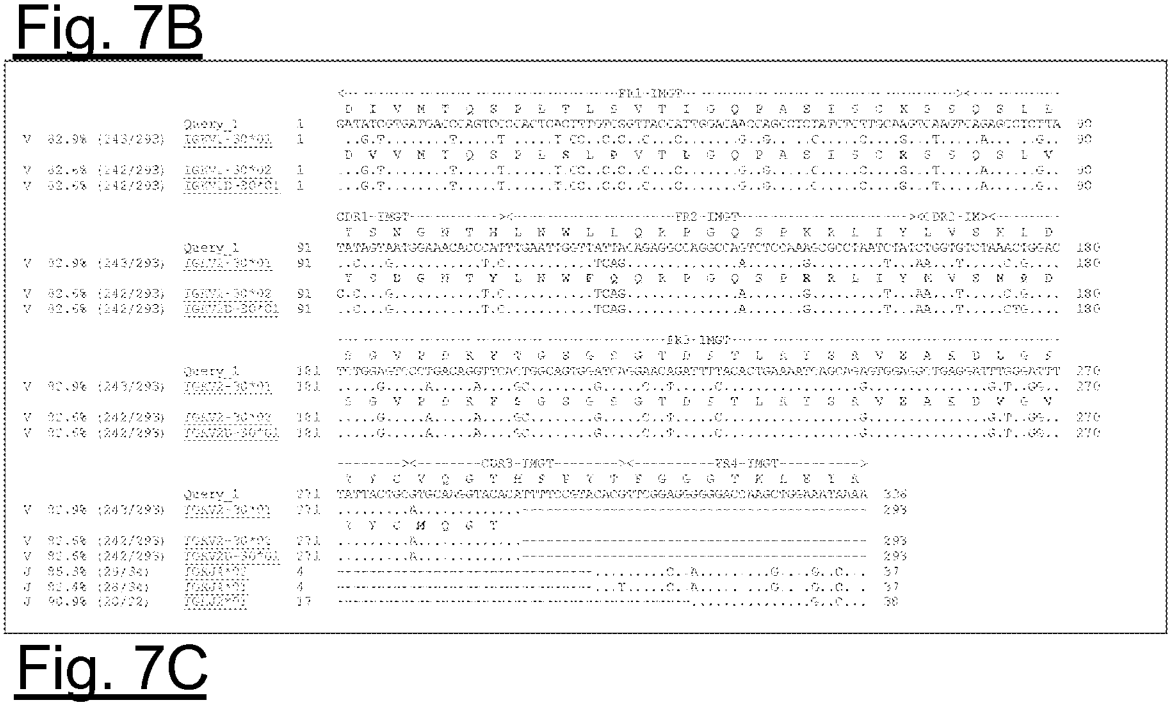

Candidate humanised sequences were selected starting from the murine one according to a classic CDR-grafting, consisting in selecting the CDR regions (defined according to the IMGT numbering scheme) of the murine sequence, and inserting them in the human germline with highest sequence similarity with the murine one in the Framework Regions (FR), as detailed in FIG. 7. FIG. 7A shows the humanisation of the 2G8 $VH_c$ sequence (SEQ ID NO: 4) obtained in Example 1 with the most homologous human germline IGHV1-46*01, accession number X92343. FIG. 7B shows the amino-acids comparison from murine $VH_c$ 2G8 (VH2G8MURINE, SEQ ID NO: 4) and the here obtained humanised VH 2G8, named H1 (VH2G(HUMANISED, SEQ ID NO: 16). FIG. 7C shows the humanisation of the 2G8 $VL_c$ sequence (SEQ ID NO: 8) with the cited most homologous human germline IGHV1-46*01. The here obtained sequence of humanised VH, named H1 (SEQ ID NO: 16) and VL, named K1 (SEQ ID ID NO: 15), are as follows:

```
H1,
                                  SEQ ID NO: 16
QVQLVQSGAEVKKPGASVKVSCKASGYTLSSYWMHWRQAP

GQGLEWMGIILPGSGSTSYAQKFQGRVTMTRDTSTSTVYM

ELSSLRSEDTAVYYCAREGWYFDVWGAGTTVTVSS

K1,
                                  SEQ ID NO: 15
DVVMTQSPLSLPVTLGQPASISCRSSQSLLYSNGNTHLNW

FQQRPGQSPRRLIYLVSNRDSGVPDRFSGSGSGTDFTLKI

SRVEAEDVGVYYCVQGTHFPYTFGGGTKLEIK
```

H1 and K1 were transfected in a high-throughput microscale system. 3 ml of CHO-S cells culture were transfected using the EXPICHO Expression system (Thermo Scientific™) according to the information supplied by the manufacturer. After one week, supernatants were collected for further analysis. The antibody production on a medium scale was carried out with the same expression system.

Supernatants containing antibodies were centrifuged, filtered 0.22 μm to remove cells and debris and batch purified by affinity chromatography using TOYOPEARL AF-rProtein A HC-650F resin (Tosoh Bioscience LLC). Antibodies were eluted with Buffer Citrate 0.1M pH 3, neutralized with an alkaline solution and dialyzed in PBS1× with slide-A-Lyzer (Thermo Scientific™). Purity of the antibody was checked by SDS-PAGE analysis that was performed under reducing/non-reducing conditions according to the standard method. Endotoxin levels were evaluated by Pierce™ LAL Chromogenic Endotoxin Quantitation Kit (Thermo Scientific™) and the presence of aggregates analysed through HPLC-SEC analysis.

The activity of the purified antibody was then tested by ELISA assay. 96-well plates were coated with 50 μg/ml Laminarin (Sigma-Aldrich, L9634) in 0.05 M carbonate buffer pH 9.6 overnight at 4° C. Nonspecific interactions were blocked with 100 μL/well blocking solution, 3% (w/v) BSA in PBS-Tween 20 (8 g/L NaCl, 0.2 g/L $KH_2PO_4$, 2.9 g/L $Na_2HPO_4 \cdot 12\ H_2O$, 0.2 g/L KCl, 0.05% (v/v) Tween 20, pH 7.4) at 37° C. for 1 h. The plates were then incubated with decreasing concentrations of hmAb 2G8_first approach (comparative purpose) (from 3.12 μg/ml to 0.003 μg/ml, each concentration was tested in triplicate) in blocking solution for 2 h at 37° C. At the same temperature and for the same time, 100 μL Goat anti-human-HRP diluted 1:1000 in blocking solution was poured in each well. After every single passage the plates were washed 5 times with PBS-Tween 20. To reveal the binding, 100 μl of 5 mg-ABTS tablet (Roche Diagnostics) dissolved in 12 ml of sodium citrate (0.05 M, pH 3) and supplemented with 1:1000 dilution hydrogen peroxide (Carlo Erba) was added and after 15, 30, 45 and 60 min the absorbance at 405 nm was measured. For the whole measuring time the plates were left in the dark. IC50 analysis of ELISA test was performed with Prism. The TEST was performed in triplicate.

The hmAb 2G8 H1/K1 was not active in an ELISA test.

Example 2B, Second Approach

Sequences obtained in Example 1, $VH_c$ and $VL_c$ sequences, SEQ ID NO: 4 and SEQ ID NO: 3, respectively, underwent CDR-grafting. Only the Framework Regions (FRW) present in the human germline gene database (ncbi.nlm.nih.gov/igblast) were analysed, according to Table 1.

TABLE 1

| Germline genes databases | Selection |
|---|---|
| Organism for query sequence | Human |
| Germline V gene Database | IMGT Human V genes (F + ORF + in-frame P) |
| Germline D gene Database | IMGT Human D genes (F + ORF) |
| Germline J gene Database | IMGT Human V genes (F + ORF) |

The obtained sequences of humanised VH, named H2 (SEQ ID NO: 18) and VL, named K2 (SEQ ID NO: 17), are as follows:

```
H2,
                                              SEQ ID NO: 18
QVQLVQSGAEVKKPGASVKVSCKASGYTLSSYWLHWVQQS

PGQGLEWMGEILPGSGSTNYAQKFQGRVTITADKSTSTAY

MELSSLRSEDTAVYYCAREGWYFDVWGAGTTVTVSS

K2,
                                              SEQ ID NO: 17
DIVMTQTPLSLSVTPGQPASISCKSSQSLLYSNGNTHLNW

FQQRPGQSPRRLIYLVSNRASGVPDRFSGSGSGTDFTLKI

SRVEAEDVGVYYCVQGTHEPYTFGGGTKLEIK
```

The obtained sequences were launched in Protein Data Bank (PDB) and compared with the sequences found to be the most similar and with an available x-ray crystallographic resolution ≤2 Å (rcsb.org). Results are reported in FIG. 8. The alignment of the three most homologous sequences emerging from PDB database analyses showed that only one amino acids was different (E50W), and for this reason it has been mutagenized inserting W in the VH sequence. Furthermore, we back mutated additional three amino acids in the VH sequence to reduce the risk of protein aggregation (M48I, R67K, V68A) and three amino acids in the VL sequence (R24K, K44R, S68T). This approach generated the following sequences of humanised VH, named H3 (SEQ ID NO: 20) and VL, named K3 (SEQ ID NO: 19):

```
H3,
                                              SEQ ID NO: 20
QVQLVQSGAEVKKPGASVKVSCKASGYTLSSYWIHWVRQA

PGQGLEWIGWILPGSGSTNYAQKFQGKATITADKSTSTAY

MELSSLRSEDTAVYYCAREGWYFDVWGQGTLVTVSS

K3,
                                              SEQ ID NO: 19
DIVMTQTPLSLSVTPGQPASISCKSSQSLLYSNGNTHLNW

YLQRPGQSPQLLIYLVSNRASGVPDRFTGSGSGTDFTLKI

SRVEAEDVGVYYCVQGTHFPYTFGGGTKVEIK
```

H3 and K3 have been expressed as a recombinant Ab. Also in this case, the antibodies were not active in an ELISA test.

Example 2C, Third Approach

The humanization approach described in Clavero-Álvarez A et al. Scientific Reports 2018; 8:14820 has been followed, resorting to statistical modelling of the variable regions of human antibody sequences. $VH_c$ and $VL_c$ regions, SEQ ID NO: 8 and SEQ ID NO: 7, were aligned according to the AHo scheme and juxtaposed, to yield a unique VH-VL sequence with gaps of length 298, using IMGT numbering scheme and Kabat numbering scheme. The two protocols differ in the choice of the CDR regions to be kept fixed: in the first case, they coincided with residues chosen for the CDR-grafting protocol above, while in the second case, CDR residues were those corresponding to the Kabat numbering scheme.

This approach, that includes residue-residue correlations both within and between heavy and light chains, strongly depends on which residues are kept fixed, as belonging to CDR regions: starting from the murine sequence, the method implies mutating one residue at a time, choosing the mutation, at any site and to any amino-acid, that yields the greatest increase in the MG-score.

This method does not guarantee to reach the highest scoring (i.e. the most humanlike sequence with the given CDRs), but it finds the local maximum closest to the initial murine sequence, with the smallest number of mutations (i.e. the shortest path to it).

The trajectories in sequence space thus produced were further analyzed with CamSol Intrinsic Server (mvsoftware-.ch.cam.ac.uk/index.php/camsolintrinsic), to check explicitly their tendency towards aggregation. Since CamSol uses local sequence information for prediction, the latter could be affected by the presence of the artificial contiguity between the C-term of the VH chain and the N-term of the VL one in the alignment used in the design step above: for this reason, we analyse separately the VH and VL chains with CamSol, and also analyse scFV constructs, with a common linker between the two chains.

This allows to separately pick, along the Kabat trajectory, the VH and VL sequences having the least tendency towards aggregation, among those that score above the murine/human threshold, and also the scFV that best copes with the requirements of having a good MG-score and a good solubility; the same is done for the other protocol, with the IMGT trajectory.

The humanization process based on the MG-score described above generated a trajectory that stopped at 42 mutations from the initial sequence in the IMGT definition of the CDRs, and at 35 mutations in the Kabat definition. The threshold between murine and human sequences is 6383 (Clavero-Álvarez A et al. 2018, cited), and we note that sequence can be considered as human starting from step 7 on both trajectories; on the other hand, the documentation of the CamSol Intrinsic tool states that regions with scores larger than 1 denote highly soluble regions, while scores smaller than −1 are indicative of poorly soluble ones. As a trade-off between the above consideration, we chose the VH sequence corresponding to sequence 19 and the VL of sequence 36 along the IMGT trajectory, and the VH of sequence 15 and VL of sequence 24 in the "Kabat" trajectory. Notice that in these latter sequences, the VHs are the same as those individually chosen before, but the VL is different, so that we end up with one choice of VH sequence and two choices of VL sequences for each trajectory. These sequences are listed below:

```
KABAT
K5,
                                        SEQ ID NO: 21
DIVMTQSPLSLPVTLGQPASISCKSSQSLLYSNGNTHLNW

YQQRPGQSPRRLIYLVSKLDSGVPDRFSGSGSGTDFTLKI

SRVEAEDVGVYYCVQGTHEPYTFGGGTKLEIK

H5,
                                        SEQ ID NO: 22
QVQLQQSGAELKKPGASVKISCKASGYTLSSYWLEWVRQR

PGQGLEWIGEILPGSGSTNYNEKFKGRATFTADTSTNTAY

MELSSLTSEDSAVYYCAREGWYFDVWGQGTTVTVSS

IMGT
K6,
                                        SEQ ID NO: 23
DIVMTQSPLSLPVTLGQPASISCRSSQSLLYSNGNTHLNW

YQQRPGQSPRRLIYLVSNRDSGVPDRFSGSGSGTDFTLKI

SRVEAEDVGVYYCMQGTHFPYTFGGGTKLEIK
```

-continued

```
H6,
                                        SEQ ID NO: 24
QVQLQQSGAELKKPGASVKISCKASGYTLSSYWIHWVRQR

PGQGLEWIGEILPGSGSTNYNEKFKGRATFTADTSTNTAY

MELSSLTSEDSAVYYCAREGWYFDVWGQGTTVTVSS

KABAT
K7,
                                        SEQ ID NO: 25
DIVMTQSPLSLPVTLGQPASISCKSSQSLLYSNGNTHLNW

YLQRPGQSPKRLIYLVSKLDSGVPDRFSGSGSGTDFTLKI

SRVEAEDVGVYYCVQGTHFPYTFGGGTKLEIK

H7,
                                        SEQ ID NO: 26
QVQLQQSGAELKKPGASVKISCKASGYTLSSYWLEWVRQR

PGQGLEWIGEILPGSGSTNYNEKFKGRATFTADTSTNTAY

MELSSLTSEDSAVYYCAREGWYFDVWGQGTTVTVSS

IMGT
K8,
                                        SEQ ID NO: 27
DIVMTQSPLSLPVTLGQPASISCKSSQSLLYSNGNTHLNW

YLQRPGQSPKRLIYLVSKRDSGVPDRFSGSGSGTDFTLKI

SRVEAEDVGVYYCMQGTHFPYTFGGGTKLEIK

H8,
                                        SEQ ID NO: 28
QVQLQQSGAELKKPGASVKISCKASGYTLSSYWIHWVRQR

PGQGLEWIGEILPGSGSTNYNEKFKGRATFTADTSTNTAY

MELSSLTSEDSAVYYCAREGWYFDVWGQGTTVTVSS
```

Among the identified and above listed sequences, only the sequence named H5/K5, when expressed as recombinant protein, showed some activity in an ELISA assay. However, the reactivity of this humanised mAb was lower than the activity observed for the murine 2G8.

Example 2D, Fourth Approach

Given the totally unsatisfying results obtained with the first, second and third state of the art approach, the authors random combined each one of the humanised VH sequences obtained with the three above reported approaches with each one of the humanised VL sequences.

Four different heavy chains (H1, H3, H5, H6) were combined with six different light chains (K1, K3, K5, K6, K7, K8), resulting in a series of humanised mAb randomly comprising the selected heavy and light chains.

The surnatants collected from the obtained humanised mAb were tested in ELISA test. Results are reported in Table 2.

TABLE 2

| Humanized mAbs | Abs 405 nm |
|---|---|
| H1 K1 | 0.35 |
| H3 K1 | 0.4 |
| H5 K1 | 3.48 |
| H5 K3 | 2.47 |
| H5 K5 | 1.61 |
| H5 K7 | 0.82 |
| H6 K1 | 0.27 |

The observed data are indicative of the fact that only antibodies comprising the 6 CDRs according to the present invention are effective in the ELISA assay, wherein antibodies that do not comprise at least one of the defined CDR do not sow the desired activity.

The activity observed with the humanised mAb comprising H5 (SEQ ID NO: 22) and K1 sequences (SEQ ID NO: 15) has been surprisingly high.

Figure 9:
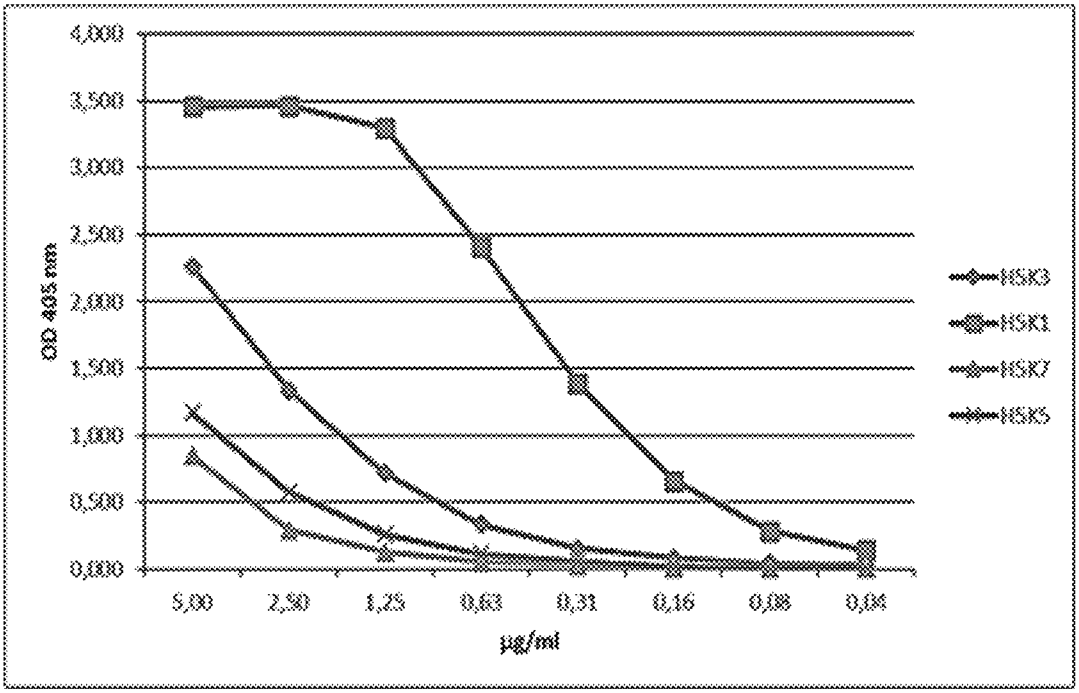
FIG. 9: ELISA assays performed by using the indicated antibodies.

Example 3: Characterization of H5/K1 Recombinant, Humanised Anti β-1,3 Glucan Antibody Four supernatants from hmAb according to the invention (H5/K3; H5/K1; H5/K7; H5/K5) were purified to confirm the data. 8 scalar dilutions, starting from 5 μg/ml, were tested. The results are shown in FIG. 9 and confirm the combination heavy:light H5/K1 being the best performer in ELISA assay.

Figure 10A:
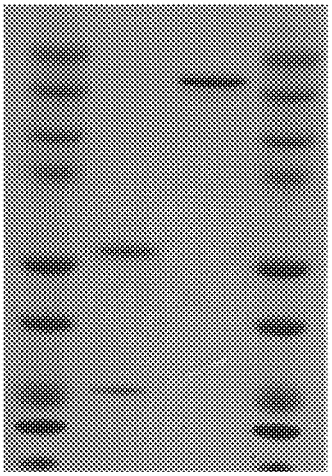
FIG. 10: Characterization of the hmAb 2G8 H5/K1 by (A) SDS-PAGE and (B) HPLC-SEC analysis.
Figure 10B:
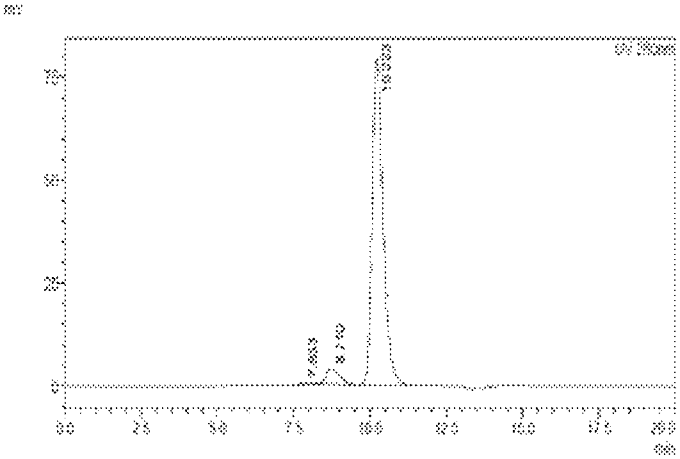

A medium scale production was executed using the EXPICHO Expression and purified by affinity chromatography as above. The structural integrity and the absence of aggregates were confirmed by SDS-PAGE (FIG. 10A) and HPLC-SEC analysis (FIG. 10B).

Figure 11:
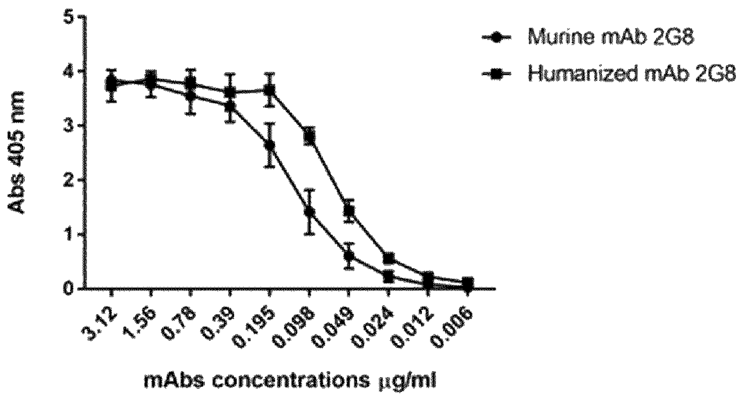
FIG. 11: ELISA assays evaluating laminarin binding.
Figure 11:
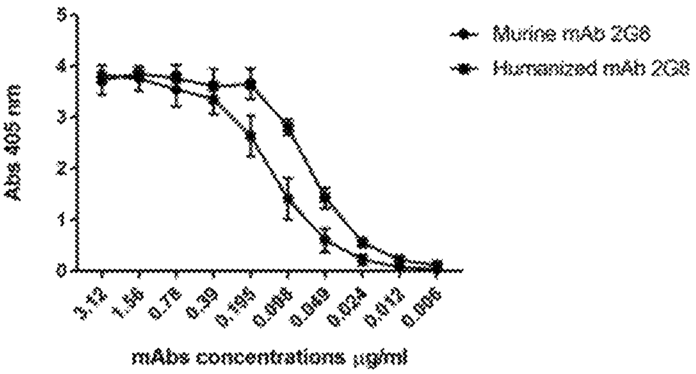

The purified humanised mAb 2G8 H5/K1 was then tested in an ELISA assay using laminarin as a target. FIG. 11 shows the activity of hmAb 2G8 H5/K1 against Laminarin compared to the murine one, the mAb 2G8 according to WO2006030318. The IC50 values of the humanised and murine mAbs estimated from these data were respectively 0.06 μg/ml and 0.120 μg/ml. Thus, the hmAb 2G8 H5/K1 performs better than the original murine one.

Example 4: Recognition of Pathogenic Fungi Expressing β-1,3-Glucan and Effect of hmAb 2G8 H5/K1 on the Same From an overnight inoculum, *C. auris* cells were washed with RPMI+MOPS (0.165 M, pH 7) and $3.0\times10^6$ cells were pelleted, suspended in Phosphate buffered saline (PBS) containing 3% (w/v) BSA (Bovine Serum Albumin-Sigma Aldrich) and put in contact with 12 μg/ml of the humanised mAb 2G8 for 1 hour at room temperature. The cells were then washed with PBS and marked with anti-human IgG FITC antibody 1:150 in PBS+3% BSA for 1 hour.

The cells were then washed and fixed with paraformaldehyde 4% in PBS 1 hour at 4° C. After fixing and washing with PBS, the pellet was suspended in 400 μl of PBS and splitted in two tubes. The samples were analysed using flow cytometry and confocal microscopy, respectively.

Figure 12A:
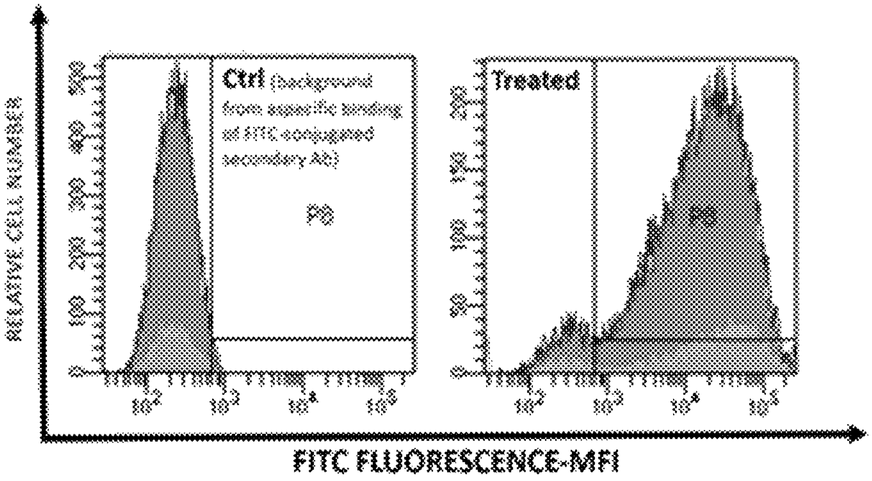
FIG. 12: (A) FITC-fluorescence signal from control and hmAb 2G8 H5/K1 treated samples. (B) fold of increase in treated versus control samples.
Figure 12B:
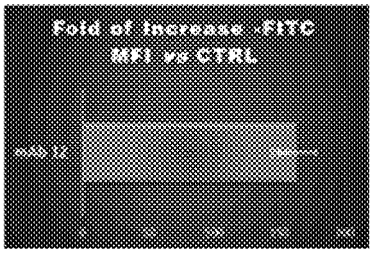

A Flow cytometer (FACScanto II, BDBioscences, Erembodegem, Belgium), equipped with three lasers (488 nm, 633 nm, 405 nm) was employed to collect and quantitate FITC fluorescence from different samples. Both autofluorescence and fluorescence derived from aspecific binding of FITC-conjugated secondary Ab were quantitated by Flow Cytometry. FIG. 12A shows fluorescence signal from control samples (on the left) and from treated samples (on the right). The histogram CTRL evaluates the background from aspecific binding of FITC-conjugated secondary Ab, enabling to fix the threshold defining the positivity for the humanised mAb H5/K1 (treated). 97% of events express the antigen (treated panel). The expression was precisely quantitated by MFI values: the fold of increase is 164, when compared to control (FIG. 12B). Light grey events in FIG. 12A histograms represent cells outside the scatter area mainly occupied by the cells: i.e. aggregates or increase in cell size (as during senescence).

Figure 13:
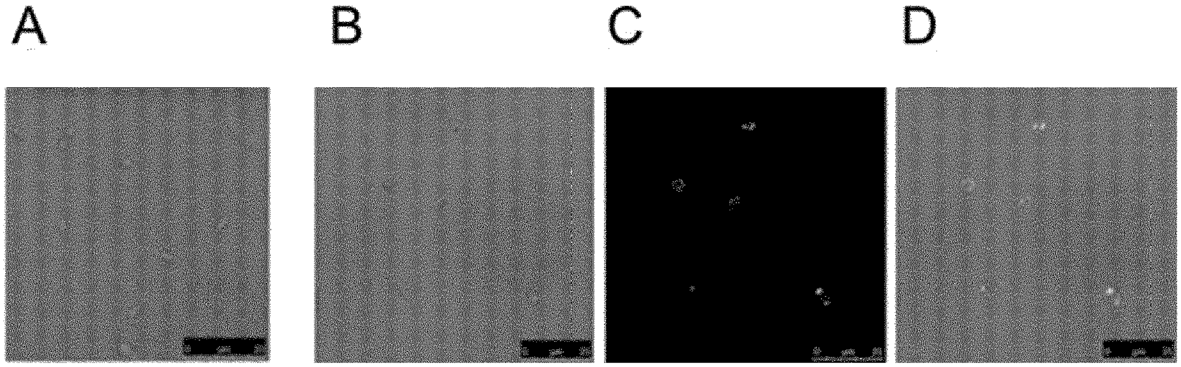
FIG. 13: exemplificative confocal images (A, B) control; (C, D) hmAb 2G8 H5/K1 treated samples.

The exemplificative confocal images, reported in FIG. 13, show the ability of the hmAb H5/K1 to recognize and bind β-1,3-glucans on the surface of *C. auris* (white dots corresponding to the FITC signal).

Example 5: Growth Inhibition Assay

The growth inhibitory activity of humanised mAb 2G8 H5/K1 was tested as reported in W. Magliani et al, Nature Biotech. 1997; 15:155-158 with some modifications. In brief, 150-250 cells of *C. auris* in 10 μl of PBS were incubated with 100 μl of humanised mAb 2G8 at 250, 100 and 50 μg/ml (each concentration was tested in triplicate) and incubated for 18 h at 37° C. The inhibition was evaluated by seeding the yeast on PDA. The plates were incubated at 37° C. for 48 h and the inhibition was calculated by count of the CFU. The assay was performed in triplicate.

Figure 14:
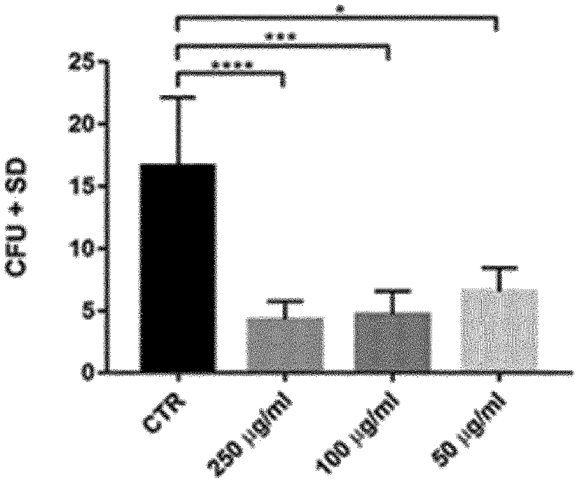
FIG. 14: Yeast cells growth inhibition in the absence (CTR) or in the presence of the indicated amount of hmAb 2G8 5H/K1.

From the CFU counts, hmAb H5/K1 provided a statistically significant effect on the inhibition of the yeast cell growth at all the doses tested (FIG. 14) ranging over 70% for 250 and 100 μg/ml and over 60% for 50 μg/ml.

Example 6: Adhesion Assay

Figure 15:
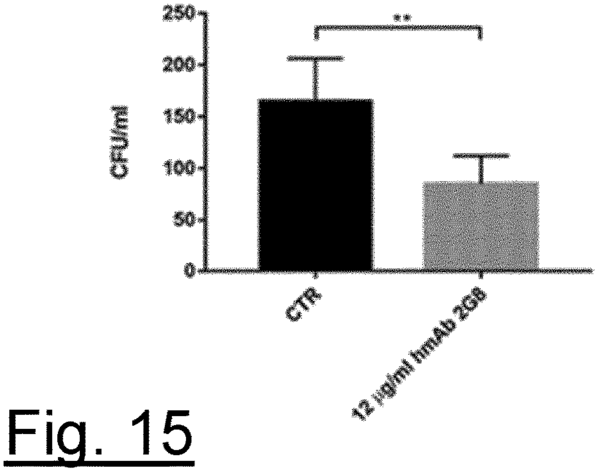
FIG. 15: Fungal adhesion to mammalian cells in the presence or in the absence (CTR) of hmAb 2G8 5H/K1.

In order to investigate the protective effect of hmAb 2G8 H5/K1 in preventing fungal adhesion to human cells commonly known to be preferred targets, *C. auris* cells were left adhering to a monolayer of HeLa cells together with the humanised mAb H5/K1, to reproduce an infection-medication scenario. $1.0\times10^4$ cervical cancer cells HeLa were suspended in RPMI+*10% FBS (pH 7) and plated in a 96-well plate for 2 hours at 37° C.+5% $CO_2$. After incubation, the cells not attached at the bottom of the wells were washed away and $1.0\times10^4$ cells of *C. auris* suspended in RPMI+MOPS (0.165 M, pH 7) were added to reach a 1:1 ratio HeLa:yeast cells. Together with the yeast, 12 μg/ml of the humanised mAb 2G8 were added. PBS was used in the control sample. The plate was left at 37° C. for 1 hour and after washing 5 times, HeLa cells were lysed with PBS 0.1% Triton X100 (15 min. RT). The suspension was plated in PDA plate and incubated at 37° C. for 48 hours. This experiment has been repeated two times in triplicate. Even when tested at a low dose, i.e. 12 μg/ml, hmAb 2G8 H5/K1 can afford a statistically significant reduction in fungal adhesion to mammalian cells of 51.5% (FIG. 15).

Example 7: Synergistic Effect, MIC Assay

To evaluate the susceptibility of *C. auris* to caspofungin, amphotericin B and their combination with hmAb 2G8, we followed the EUCAST antifungal MIC method (EUCAST E.DEF. 7.3). Antifungal drugs were purchased from Sigma-Aldrich.

The caspofungin and amphotericin B range concentrations analysed were reported in EUCAST document. Those concentrations were tested alone and in combination with 0.25, 2.5, 25 and 250 μg/ml of humanised antibody.

The plates microdilution and the yeast inoculum were prepared as reported in EUCAST document. The wells with 100 μl of 2× final antifungal drugs concentration in RPMI 2% G medium were inoculated with 100 μl ($1\text{-}5\times10^5$ CFU/ml) of yeast suspension of *C. auris*. The monoclonal antibody was added to the samples of yeast suspension to test the combination drug-antibody. The plates were incubated at 37° C. for 24 and 48 hours and read after incubation at 405 nm. The assays were performed in triplicate.

Figures 16A, 16B, 16C, 16D:
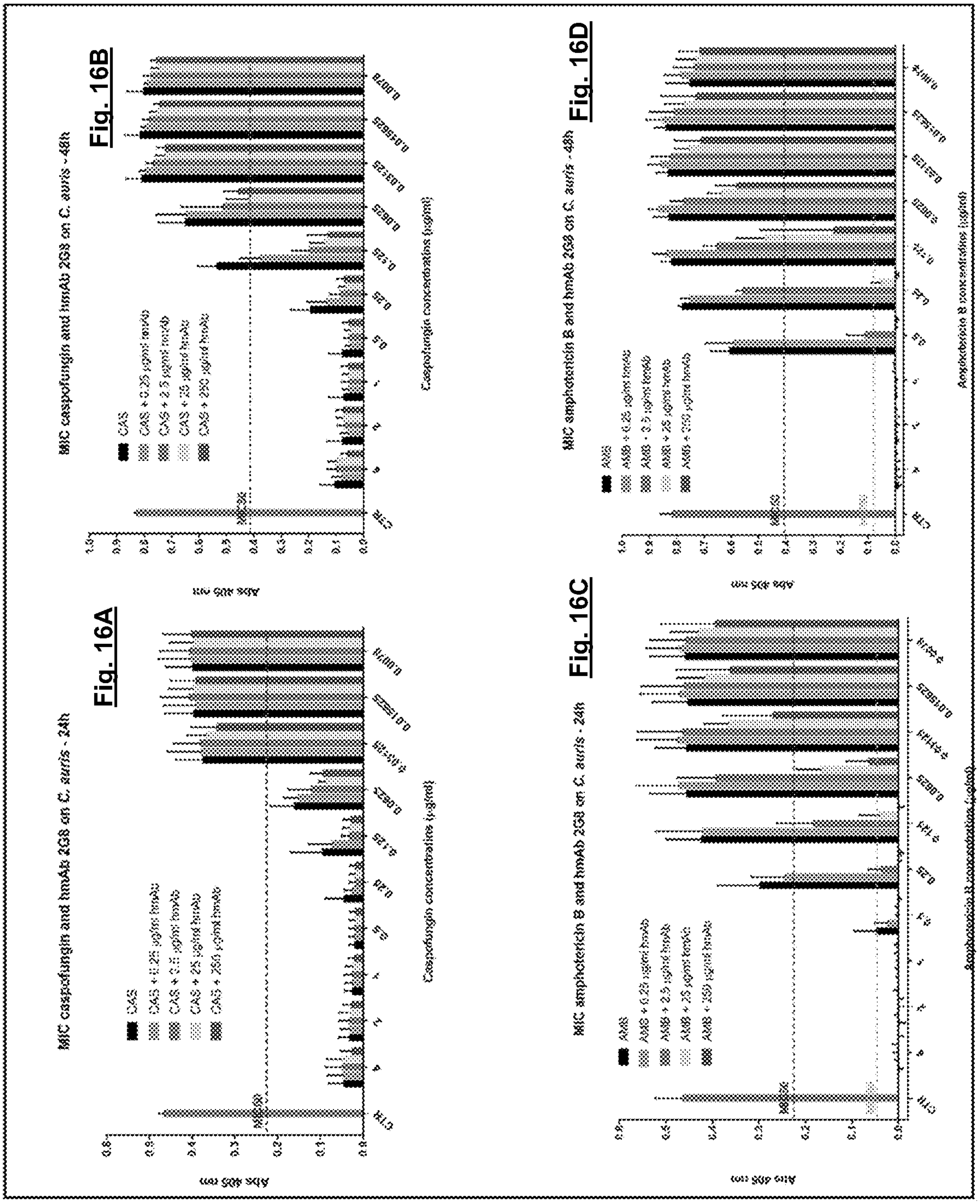
FIG. 16: MIC assays of caspofungin alone (CAS) and in combination with different concentrations of humanised mAb 2G8 at 24 h (A) and 48 h (B). MIC assays of amphotericin B alone (AMB) and in combination with different concentrations of humanised mAb 2G8 at 24 (C) and 48 (D) hours.

The results are reported in FIG. 16.

As reported in EUCAST, echinocandins' MIC50 is the lowest drug concentration giving inhibition of ≥50% of that of the drug-free control (dotted line). For amphotericin B, MIC50 is the same as for echinocandins while MIC90 is considered as the lowest concentration giving a growth inhibition of ≥90% of that of the drug-free control (dotted bold line). After 24 hours (A) the MIC breakpoints of caspofungin alone and in combination with hmAb 2G8 are fixed at 0.0625 µg/ml. At 48 hours (B), MIC50 is set at 0.25 µg/ml of caspofungin alone while at 0.125 µg/ml if in combination with 25 and 250 µg/ml of hmAb 2G8. This shows a reduction of 1 dilution of caspofungin concentration (from 0.25 to 0.125 µg/ml). For what concerns amphotericin B, at 24 hours (C), the drug alone has a MIC50 and MIC90 at 0.5 µg/ml whereas, with 2.5 µg/ml of hmAb 2G8, MIC50 and 90 are respectively at 0.125 µg/ml and 0.25 µg/ml. With 25 and 250 µg/ml of hmAb 2G8, MIC50 shifts at 0.0625 and MIC90 at 0.125 µg/ml. At 48 hours (D), amphotericin B alone has its MIC50 and 90 at 1 µg/ml. With 2.5 µg/ml of hmAb, MIC90 is the same as for the AMB alone but MIC50 is at 0.5 µg/ml. The combination with 25 µg/ml of hmAb fixes MIC50 and 90 together at 0.25 µg/ml while with 250 µg/ml of the humanised mAb. MIC90 is at 0.25 µg/ml and MIC50 at 0.125 µg/ml.

Example 8: Synergistic Effect, Time-Kill Curve

To support and deepen the data coming from MIC assays, a time-kill curve was elaborated to evaluate how the hmAb 2G8 combined with caspofungin or amphotericin B could improve their basal activity on *C. auris.*

Figure 17:
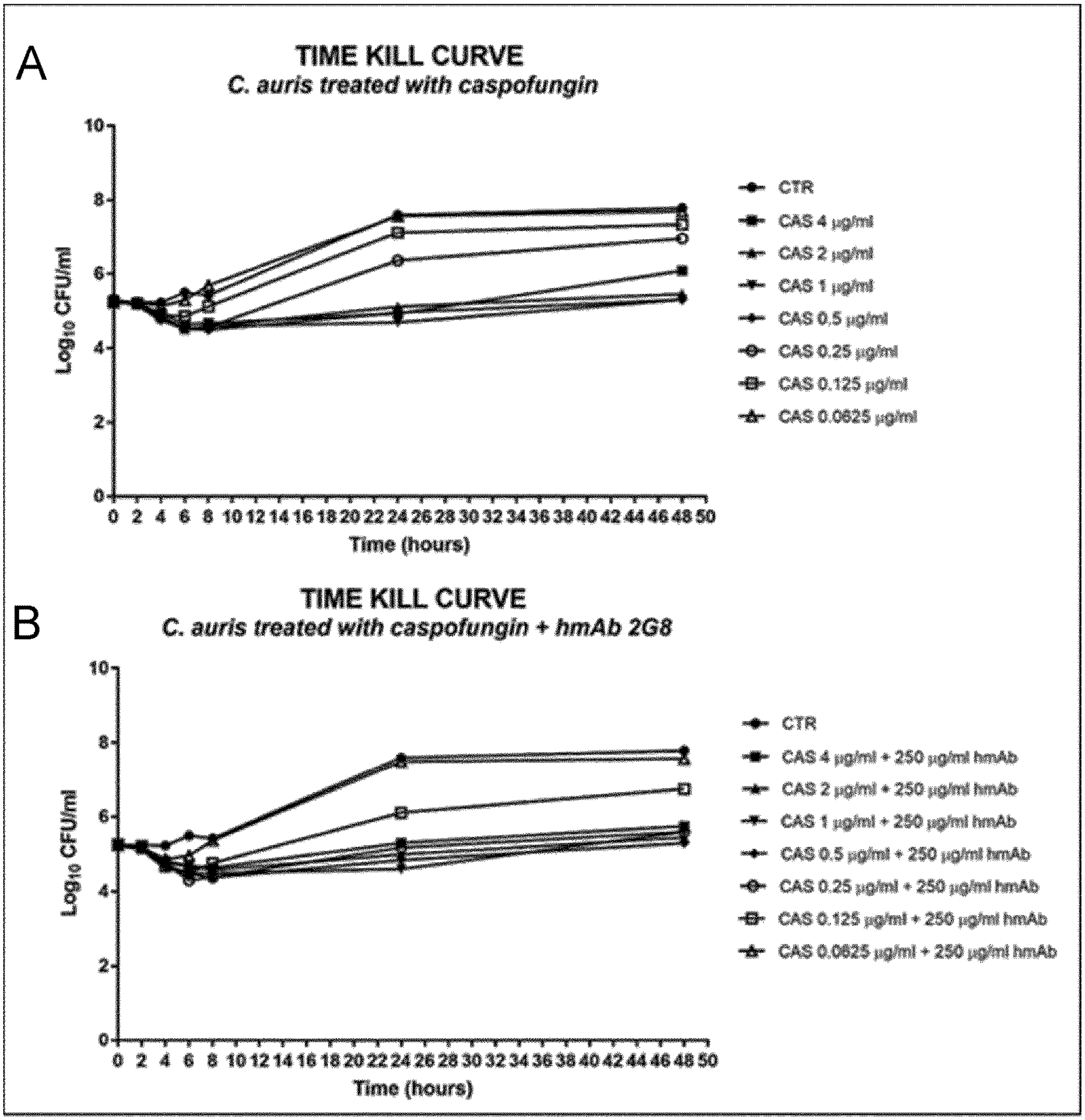
FIG. 17: time-kill curve of caspofungin alone (A) or in combination with hmAb 2G8 (B).

Results are reported in FIG. 17. At 24 h and 48 h, when caspofungin efficiency at 0.25 and 0.125 µg/ml starts decreasing, the presence of hmAb ameliorated the fungistatic activity. In particular with 0.125 µg/ml caspofungin, it resulted in a recovery slower than the one with CAS alone while the combination of 0.25 µg/ml+250 µg/ml of hmAb 2G8 H5K1 maintained a constant trend all over time.

Table 3 shows the improvement of the fungistatic effect thanks to the presence of hmAb 2G8 H5K1: the combination of CAS 0.25 µg/ml and hmAb 2G8 H5K1 ensures more than 1 log difference both at 24 and 48 hours and the combination with 0.125 µg/ml shows more than 1 log difference at 24 hours and more than half log at 48 hours.

TABLE 3

| | 24 h | 48 h |
|---|---|---|
| CAS 0.25 µg/ml | −1.11 | −1.71 |
| CAS 0.25 µg/ml + hmAb 2G8 | −0.02 | −0.46 |
| CAS 0.125 µg/ml | −1.88 | −2.10 |
| CAS 0.125 µg/ml + hmAb 2G8 | −0.87 | −1.51 |

Figure 18:
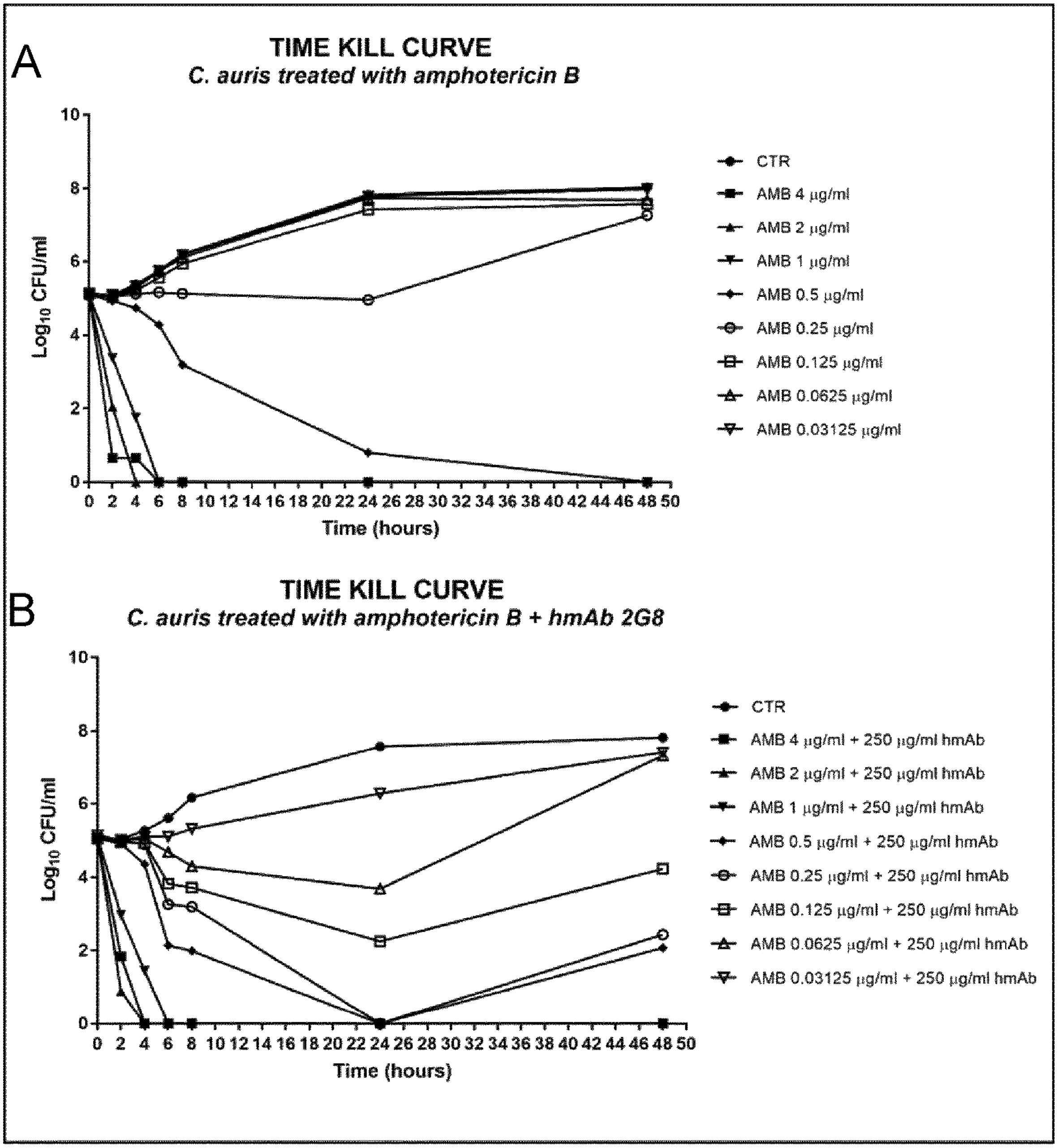
FIG. 18: time-kill curve of amphotericin B alone (A) or in combination with hmAb 2G8 (B).

Amphotericin B efficiency starts decreasing at 0.25 µg/ml. The fungicidal activity of Amphotericin B alone is obtained after 24 hours but, when administered in combination with hmAb 2G8 H5K1 the effect arises at 6 hours, as reported in table 4 and in FIG. 18. Moreover, the combination shows a better effect at almost each concentration of Amphotericin B, the synergistic effect is still ≥3 log at 24 h with 0.25 µg/ml Amphotericin B (table 4).

TABLE 4

| | 0 h | 2 h | 4 h | 6 h | 8 h | 24 h | 48 h |
|---|---|---|---|---|---|---|---|
| AMB 4 µg/ml | 0.06 | ≥3 Log | ≥3 Log | ≥3 Log | ≥3 Log | ≥3 Log | ≥3 Log |
| AMB 4 + hmAb 2G8 | 0.08 | ≥3 Log | ≥3 Log | ≥3 Log | ≥3 Log | ≥3 Log | ≥3 Log |
| AMB 2 µg/ml | 0.05 | ≥3 Log | ≥3 Log | ≥3 Log | ≥3 Log | ≥3 Log | ≥3 Log |
| AMB 2 + hmAb 2G8 | 0.1 | ≥3 Log | ≥3 Log | ≥3 Log | ≥3 Log | ≥3 Log | ≥3 Log |
| AMB 1 µg/ml | 0.05 | 1.77 | ≥3 Log | ≥3 Log | ≥3 Log | ≥3 Log | ≥3 Log |
| AMB 1 + hmAb 2G8 | 0.05 | 2.16 | ≥3 Log | ≥3 Log | ≥3 Log | ≥3 Log | ≥3 Log |
| AMB 0.5 µg/ml | 0.05 | 0.21 | 0.41 | 0.86 | 1.95 | ≥3 Log | ≥3 Log |
| AMB 0.5 + hmAb 2G8 | 0.09 | 0.22 | 0.78 | ≥3 Log | ≥3 Log | ≥3 Log | ≥3 Log |
| AMB 0.25 µg/ml | 0.07 | 0.1 | 0.02 | −0.02 | 0.02 | 0.19 | −2.13 |
| AMB 0.25 + hmAb 2G8 | 0.11 | 0.13 | 0.25 | 1.88 | 1.95 | ≥3 Log | 2.66 |
| AMB 0.125 µg/ml | 0.01 | 0.11 | −0.07 | −0.42 | −0.80 | −2.28 | −2.44 |
| AMB 0.125 + hmAb 2G8 | 0.09 | 0.20 | 0.21 | 1.31 | 1.42 | 2.88 | 0.91 |
| AMB 0.0625 µg/ml | 0.00 | 0.07 | −0.14 | −0.59 | −0.97 | −2.59 | −2.57 |
| AMB 0.0625 + hmAb 2G8 | 0.09 | 0.15 | 0.09 | 0.46 | 0.84 | 1.45 | −2.17 |
| AMB 0.03125 µg/ml | 0.01 | 0.05 | −0.19 | −0.62 | −1.04 | −2.65 | −2.85 |
| AMB 0.03125 + hmAb 2G8 | 0.07 | 0.13 | 0.01 | 0.03 | −0.18 | −1.14 | −2.26 |

According to the standardized method (Pfaller et al, Clin Microbiol Rev. 2004), the synergic action between two agents is revealed with a difference ≥2 log in their respective growth decrease after 24 hours. As showed in table 5, it is evident the strong synergy between amphotericin b and the humanised mAb 2G8 H5K1.

TABLE 5

| | 24 h | 48 h |
|---|---|---|
| Δ log A MB 0.25 · A MB 0.25 + hmAb 2G8 | 4.95 | 4.79 |
| Δ log A MB 0.125 · A MB 0.125 + hmAb 2G8 | 5.16 | 3.35 |
| Δ log A MB 0.0625 · A MB 0.0625 + hmAb 2G8 | 4.04 | 0.4 |

The invention claimed is:

1. A humanized antibody or antigen-binding fragment thereof which has specificity for β-1,3 glucans of pathogenic fungi, comprising a heavy chain variable region (VH) comprising the amino acid sequence of SEQ ID NO: 22 and a light chain variable region (VL) comprising the amino acid sequence of SEQ ID NO: 15.

2. An isolated polynucleotide comprising a nucleotide sequence encoding the humanized antibody or antigen-binding fragment thereof of claim 1.

3. A cloning or expression vector comprising the polynucleotide of claim 2.

4. A host cell comprising the cloning or expression vector of claim 3.

5. A pharmaceutical composition comprising the humanized antibody or antigen-binding fragment thereof of claim 1, in combination with one or more of a pharmaceutically acceptable excipient, diluent or carrier.

6. A method of treating fungal infection in a subject in need thereof comprising administering to the subject an effective amount of the humanized antibody or antigen-binding fragment thereof of claim 1 in combination with an effective amount of one or more antifungal agents.

7. The method of claim 6, wherein said one or more antifungal agent comprises echinocandins and/or a polyene macrolide.

8. A pharmaceutical composition comprising a) the humanized antibody or antigen-binding fragment thereof of claim 1 and b) one or more antifungal agents with one or more of a pharmaceutically acceptable excipient, diluent or carrier.

9. A method of treating fungal infection in a subject in need thereof comprising administering to the subject an effective amount of the humanized antibody or antigen-binding fragment thereof of claim 1.

10. The method of claim 6, wherein said infection is mediated by pathogenic fungi.

11. The method of claim 10, wherein said infection is a subcutaneous mycoses.

12. The method of claim 11, wherein the subcutaneous mycoses is selected from candidiasis, aspergillosis, cryptococcosis, dermatomycoses, and sporotrichosis.

13. The antibody or antigen-binding fragment thereof of claim 1, which is an antigen-binding fragment selected from Fab, F(ab')2, Fv, and scFv.

14. The antibody or antigen-binding fragment thereof of claim 1, which is a full-length IgG class antibody.

15. An antibody or antigen-binding fragment thereof which has specificity for β-1,3 glucans of pathogenic fungi comprising a heavy chain variable region (VH) and a light chain variable region (VL), wherein the VH comprises (i) a CDRH1 comprising the amino acid sequence SYWLE (SEQ ID NO: 10), (ii) a CDRH2 comprising the amino acid sequence EILPGSGSTNYNEKFKG (SEQ ID NO: 12), and (iii) a CDRH3 comprising the amino acid sequence EGWYFDV (SEQ ID NO: 14), wherein the VL comprises (iv) a CDRL1 comprising the amino acid sequence QSLLYSNGNTH (SEQ ID NO: 9), (v) a CDRL2 comprising the amino acid sequence LVS (SEQ ID NO: 11), and (vi) a CDRL3 comprising the amino acid sequence VQGTHFPYT (SEQ ID NO: 13), and wherein the VH and VL comprises an amino acid sequence having at least 95% identity to SEQ ID NO: 22 and 15, respectively.

16. The antibody or antigen-binding fragment thereof of claim 15, which is an antigen-binding fragment selected from Fab, F(ab')2, Fv, and scFv.

17. The antibody or antigen-binding fragment thereof of claim 15, which is a full-length IgG class antibody.

18. The antibody or antigen-binding fragment thereof of claim 15, wherein the VH comprises the amino acid sequence of SEQ ID NO: 22.

* * * * *

SEQUENCE LISTING

<160> NUMBER OF SEQ ID NOS: 99

<210> SEQ ID NO 1

<211> LENGTH: 121
<212> TYPE: PRT
<213> ORGANISM: Mus musculus

<400> SEQUENCE: 1

Asp Ile Val Met Thr Gln Ser Pro Leu Thr Leu Ser Val Thr Ile Gly
1 5 10 15

Gln Pro Ala Ser Ile Ser Cys Lys Ser Ser Gln Ser Leu Leu Tyr Ser
20 25 30

Asn Gly Asn Thr His Leu Asn Trp Leu Leu Gln Arg Pro Gly Gln Ser
35 40 45

Pro Lys Arg Leu Ile Tyr Leu Val Ser Lys Leu Asp Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Leu Gly Phe Tyr Tyr Cys Val Gln Gly
85 90 95

Thr His Phe Pro Tyr Thr Phe Gly Gly Gly Thr Lys Leu Glu Ile Lys
100 105 110

Arg Ala Asp Ala Ala Pro Thr Val Ser
115 120

<210> SEQ ID NO 2
<211> LENGTH: 125
<212> TYPE: PRT
<213> ORGANISM: Mus musculus

<400> SEQUENCE: 2

Leu Gln Gln Ser Gly Ala Glu Leu Met Lys Pro Gly Ala Ser Val Lys
1 5 10 15

Ile Ser Cys Lys Ala Thr Gly Tyr Thr Leu Ser Ser Tyr Trp Leu Glu
20 25 30

Trp Val Lys Gln Arg Pro Gly His Gly Leu Glu Trp Ile Gly Glu Ile
35 40 45

Leu Pro Gly Ser Gly Ser Thr Asn Tyr Asn Glu Lys Phe Lys Gly Lys
50 55 60

Ala Thr Phe Thr Ala Asp Thr Ser Ser Asn Thr Ala Tyr Met Gln Leu
65 70 75 80

Ser Ser Leu Thr Ser Glu Asp Ser Ala Val Tyr Tyr Cys Ala Arg Glu
85 90 95

Gly Trp Tyr Phe Asp Val Trp Gly Ala Gly Thr Thr Val Thr Val Ser
100 105 110

Ser Ala Lys Thr Thr Pro Pro Ser Val Tyr Pro Leu Ala
115 120 125

<210> SEQ ID NO 3
<211> LENGTH: 335
<212> TYPE: DNA
<213> ORGANISM: Mus musculus

<400> SEQUENCE: 3
gatatcgtga tgacccagtc cccactcact ttgtcggtta ccattggaca accagcctct 60
atctcttgca agtcaagtca gagcctctta tatagtaatg gaaacaccca tttgaattgg 120
ttattacaga ggccaggcca gtctccaaag cgcctaatct atctggtgtc taaactggac 180
tctggagtcc ctgacaggtt cactggcagt ggatcaggaa cagattttac actgaaaata 240
gcagagtgga ggctgaggat ttgggatttt attactgcgt gcaaggtaca cattttccgt 300
acacgttcgg aggggggacc aagctggaaa taaaa 335

<210> SEQ ID NO 4
<211> LENGTH: 116
<212> TYPE: PRT
<213> ORGANISM: Mus musculus

<400> SEQUENCE: 4

Gln Val Gln Leu Gln Gln Ser Gly Ala Glu Leu Met Lys Pro Gly Ala
1 5 10 15

Ser Val Lys Ile Ser Cys Lys Ala Thr Gly Tyr Thr Leu Ser Ser Tyr
20 25 30

Trp Leu Glu Trp Val Lys Gln Arg Pro Gly His Gly Leu Glu Trp Ile
35 40 45

Gly Glu Ile Leu Pro Gly Ser Gly Ser Thr Asn Tyr Asn Glu Lys Phe
50 55 60

Lys Gly Lys Ala Thr Phe Thr Ala Asp Thr Ser Ser Asn Thr Ala Tyr
65 70 75 80

Met Gln Leu Ser Ser Leu Thr Ser Glu Asp Ser Ala Val Tyr Tyr Cys
85 90 95

Ala Arg Glu Gly Trp Tyr Phe Asp Val Trp Gly Ala Gly Thr Thr Val
100 105 110

Thr Val Ser Ser
115

<210> SEQ ID NO 5
<211> LENGTH: 363
<212> TYPE: DNA
<213> ORGANISM: Mus musculus

<400> SEQUENCE: 5
gatatcgtga tgacccagtc cccactcact ttgtcggtta ccattggaca accagcctct 60
atctcttgca agtcaagtca gagcctctta tatagtaatg gaaacaccca tttgaattgg 120
ttattacaga ggccaggcca gtctccaaag cgcctaatct atctggtgtc taaactggac 180
tctggagtcc ctgacaggtt cactggcagt ggatcaggaa cagattttac actgaaaatc 240
agcagagtgg aggctgagga tttgggattt tattactgcg tgcaaggtac acattttccg 300
tacacgttcg gaggggggac caagctggaa ataaaacggg ctgatgctgc accaactgta 360
tcc 363

<210> SEQ ID NO 6
<211> LENGTH: 375
<212> TYPE: DNA
<213> ORGANISM: Mus musculus

<400> SEQUENCE: 6
ctgcagcagt ctggcgctga gctgatgaag cctggggcct cagtgaagat atcctgcaag 60
gctactggct acacactcag tagctactgg ctagagtggg taaagcagag gcctggacat 120
ggccttgagt ggattggaga gattttacct ggaagtggta gtactaacta caatgagaag 180
ttcaagggca aggccacatt cactgcagat acatcctcca acacagccta catgcaactc 240
agcagcctga catctgagga ctctgccgtc tattactgtg caagagaggg ttggtacttc 300
gatgtctggg gcgcagggac cacggtcacc gtctcctcag ccaaaacaac acccccatca 360
gtctatccac tggcc 375

<210> SEQ ID NO 7
<211> LENGTH: 112
<212> TYPE: PRT
<213> ORGANISM: Mus musculus

<400> SEQUENCE: 7

Asp Ile Val Met Thr Gln Ser Pro Leu Thr Leu Ser Val Thr Ile Gly
1 5 10 15

Gln Pro Ala Ser Ile Ser Cys Lys Ser Ser Gln Ser Leu Leu Tyr Ser
20 25 30

Asn Gly Asn Thr His Leu Asn Trp Leu Leu Gln Arg Pro Gly Gln Ser
35 40 45

Pro Lys Arg Leu Ile Tyr Leu Val Ser Lys Leu Asp Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Leu Gly Phe Tyr Tyr Cys Val Gln Gly
85 90 95

Thr His Phe Pro Tyr Thr Phe Gly Gly Gly Thr Lys Leu Glu Ile Lys
100 105 110

<210> SEQ ID NO 8
<211> LENGTH: 347
<212> TYPE: DNA
<213> ORGANISM: Mus musculus

<400> SEQUENCE: 8
caggtccagc tgcagcagtc tggcgctgag ctgatgaagc ctggggcctc agtgaagata 60
tcctgcaagg ctactggcta cacactcagt agctactggc tagagtgggt aaagcagagg 120
cctggacatg gccttgagtg gattggagag attttacctg gaagtggtag tactaactac 180
aatgagaagt tcaagggcaa ggccacattc actgcagata catcctccaa cacagcctac 240
atgcaactca gcagcctgac atctgaggac tctgccgtct attactgtgc aagagagggt 300
tggtacttcg atgtctgggg cgcagggacc acggtcaccg tctcctc 347

<210> SEQ ID NO 9
<211> LENGTH: 11
<212> TYPE: PRT
<213> ORGANISM: Mus musculus

<400> SEQUENCE: 9

Gln Ser Leu Leu Tyr Ser Asn Gly Asn Thr His
1 5 10

<210> SEQ ID NO 10
<211> LENGTH: 5
<212> TYPE: PRT
<213> ORGANISM: Mus musculus

<400> SEQUENCE: 10

Ser Tyr Trp Leu Glu
1 5

<210> SEQ ID NO 11
<211> LENGTH: 3
<212> TYPE: PRT
<213> ORGANISM: Mus musculus

<400> SEQUENCE: 11

Leu Val Ser
1

<210> SEQ ID NO 12
<211> LENGTH: 17
<212> TYPE: PRT
<213> ORGANISM: Mus musculus

<400> SEQUENCE: 12

Glu Ile Leu Pro Gly Ser Gly Ser Thr Asn Tyr Asn Glu Lys Phe Lys
1               5                   10                  15

Gly

<210> SEQ ID NO 13
<211> LENGTH: 9
<212> TYPE: PRT
<213> ORGANISM: Mus musculus

<400> SEQUENCE: 13

Val Gln Gly Thr His Phe Pro Tyr Thr
1               5

<210> SEQ ID NO 14
<211> LENGTH: 7
<212> TYPE: PRT
<213> ORGANISM: Mus musculus

<400> SEQUENCE: 14

Glu Gly Trp Tyr Phe Asp Val
1               5

<210> SEQ ID NO 15
<211> LENGTH: 112
<212> TYPE: PRT
<213> ORGANISM: Artificial Sequence
<220> FEATURE:
<223> OTHER INFORMATION: VL-K1

<400> SEQUENCE: 15

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Tyr Ser
            20                  25                  30

Asn Gly Asn Thr His Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Tyr Thr Phe Gly Gly Gly Thr Lys Leu Glu Ile Lys
            100                 105                 110

<210> SEQ ID NO 16
<211> LENGTH: 116
<212> TYPE: PRT
<213> ORGANISM: Artificial Sequence
<220> FEATURE:
<223> OTHER INFORMATION: VH-H1

<400> SEQUENCE: 16

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Ser Ser Tyr
            20                  25                  30

Trp Met His Trp Val Arg Gln Ala Pro Gly Gln Gly Leu Glu Trp Met
        35                  40                  45

Gly Ile Ile Leu Pro Gly Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Gly Trp Tyr Phe Asp Val Trp Gly Ala Gly Thr Thr Val
            100                 105                 110

Thr Val Ser Ser
        115


<210> SEQ ID NO 17
<211> LENGTH: 112
<212> TYPE: PRT
<213> ORGANISM: Artificial Sequence
<220> FEATURE:
<223> OTHER INFORMATION: VL-K2

<400> SEQUENCE: 17

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Asn Thr His Leu Asn Trp Phe Gln Gln Arg Pro Gly Gln Ser
        35                  40                  45

Pro Arg Arg Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Tyr Thr Phe Gly Gly Gly Thr Lys Leu Glu Ile Lys
            100                 105                 110


<210> SEQ ID NO 18
<211> LENGTH: 116
<212> TYPE: PRT
<213> ORGANISM: Artificial Sequence
<220> FEATURE:
<223> OTHER INFORMATION: VH-H2

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Ser Ser Tyr
            20                  25                  30

Trp Leu His Trp Val Gln Gln Ser Pro Gly Gln Gly Leu Glu Trp Met
        35                  40                  45

Gly Glu Ile Leu Pro Gly Ser Gly Ser Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80
```

Met Glu Leu Ser Ser Leu Arg Ser Glu Asp Thr Ala Val Tyr Tyr Cys
85 90 95

Ala Arg Glu Gly Trp Tyr Phe Asp Val Trp Gly Ala Gly Thr Thr Val
100 105 110

Thr Val Ser Ser
115

<210> SEQ ID NO 19
<211> LENGTH: 112
<212> TYPE: PRT
<213> ORGANISM: Artificial Sequence
<220> FEATURE:
<223> OTHER INFORMATION: VL-K3

<400> SEQUENCE: 19

Asp Ile Val Met Thr Gln Thr Pro Leu Ser Leu Ser Val Thr Pro Gly
1 5 10 15

Gln Pro Ala Ser Ile Ser Cys Lys Ser Ser Gln Ser Leu Leu Tyr Ser
20 25 30

Asn Gly Asn Thr His Leu Asn Trp Tyr Leu Gln Arg Pro Gly Gln Ser
35 40 45

Pro Gln Leu Leu Ile Tyr Leu Val Ser Asn Arg Ala Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Val Gly Val Tyr Tyr Cys Val Gln Gly
85 90 95

Thr His Phe Pro Tyr Thr Phe Gly Gly Gly Thr Lys Val Glu Ile Lys
100 105 110

<210> SEQ ID NO 20
<211> LENGTH: 116
<212> TYPE: PRT
<213> ORGANISM: Artificial Sequence
<220> FEATURE:
<223> OTHER INFORMATION: VH-H3

<400> SEQUENCE: 20

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Leu Ser Ser Tyr
20 25 30

Trp Ile His Trp Val Arg Gln Ala Pro Gly Gln Gly Leu Glu Trp Ile
35 40 45

Gly Trp Ile Leu Pro Gly Ser Gly Ser Thr Asn Tyr Ala Gln Lys Phe
50 55 60

Gln Gly Lys Ala Thr Ile Thr Ala Asp Lys Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Glu Gly Trp Tyr Phe Asp Val Trp Gly Gln Gly Thr Leu Val
100 105 110

Thr Val Ser Ser
115

<210> SEQ ID NO 21
<211> LENGTH: 112
<212> TYPE: PRT

```
<213> ORGANISM: Artificial Sequence
<220> FEATURE:
<223> OTHER INFORMATION: VL-K5

<400> SEQUENCE: 21

Asp Ile Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asn Gly Asn Thr His Leu Asn Trp Tyr Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Tyr Thr Phe Gly Gly Gly Thr Lys Leu Glu Ile Lys
            100                 105                 110


<210> SEQ ID NO 22
<211> LENGTH: 116
<212> TYPE: PRT
<213> ORGANISM: Artificial Sequence
<220> FEATURE:
<223> OTHER INFORMATION: VH-H5

<400> SEQUENCE: 22

Gln Val Gln Leu Gln Gln Ser Gly Ala Glu Leu Lys Lys Pro Gly Ala
1               5                   10                  15

Ser Val Lys Ile Ser Cys Lys Ala Ser Gly Tyr Thr Leu Ser Ser Tyr
            20                  25                  30

Trp Leu Glu Trp Val Arg Gln Arg Pro Gly Gln Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Arg Ala Thr Phe Thr Ala Asp Thr Ser Thr Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Gly Trp Tyr Phe Asp Val Trp Gly Gln Gly Thr Thr Val
            100                 105                 110

Thr Val Ser Ser
        115


<210> SEQ ID NO 23
<211> LENGTH: 112
<212> TYPE: PRT
<213> ORGANISM: Artificial Sequence
<220> FEATURE:
<223> OTHER INFORMATION: VL-K6

<400> SEQUENCE: 23

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Tyr Ser
            20                  25                  30

Asn Gly Asn Thr His Leu Asn Trp Tyr Gln Gln Arg Pro Gly Gln Ser
        35                  40                  45
```

```
Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Phe Pro Tyr Thr Phe Gly Gly Gly Thr Lys Leu Glu Ile Lys
            100                 105                 110


<210> SEQ ID NO 24
<211> LENGTH: 116
<212> TYPE: PRT
<213> ORGANISM: Artificial Sequence
<220> FEATURE:
<223> OTHER INFORMATION: VH-H6

<400> SEQUENCE: 24

Gln Val Gln Leu Gln Gln Ser Gly Ala Glu Leu Lys Lys Pro Gly Ala
1               5                   10                  15

Ser Val Lys Ile Ser Cys Lys Ala Ser Gly Tyr Thr Leu Ser Ser Tyr
            20                  25                  30

Trp Ile His Trp Val Arg Gln Arg Pro Gly Gln Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Arg Ala Thr Phe Thr Ala Asp Thr Ser Thr Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Gly Trp Tyr Phe Asp Val Trp Gly Gln Gly Thr Thr Val
            100                 105                 110

Thr Val Ser Ser
        115


<210> SEQ ID NO 25
<211> LENGTH: 112
<212> TYPE: PRT
<213> ORGANISM: Artificial Sequence
<220> FEATURE:
<223> OTHER INFORMATION: VL-K7

<400> SEQUENCE: 25

Asp Ile Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asn Gly Asn Thr His Leu Asn Trp Tyr Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Tyr Thr Phe Gly Gly Gly Thr Lys Leu Glu Ile Lys
            100                 105                 110
```

<210> SEQ ID NO 26
<211> LENGTH: 116
<212> TYPE: PRT
<213> ORGANISM: Artificial Sequence
<220> FEATURE:
<223> OTHER INFORMATION: VH-H7

<400> SEQUENCE: 26

Gln Val Gln Leu Gln Gln Ser Gly Ala Glu Leu Lys Lys Pro Gly Ala
1               5                   10                  15

Ser Val Lys Ile Ser Cys Lys Ala Ser Gly Tyr Thr Leu Ser Ser Tyr
            20                  25                  30

Trp Leu Glu Trp Val Arg Gln Arg Pro Gly Gln Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Arg Ala Thr Phe Thr Ala Asp Thr Ser Thr Asn Thr Ala Tyr
65                  70                  75                  80

Met Glu Leu Ser Ser Leu Thr Ser Glu Asp Ser Ala Val Tyr Tyr Cys
                85                  90                  95

Ala Arg Glu Gly Trp Tyr Phe Asp Val Trp Gly Gln Gly Thr Thr Val
            100                 105                 110

Thr Val Ser Ser
        115

<210> SEQ ID NO 27
<211> LENGTH: 112
<212> TYPE: PRT
<213> ORGANISM: Artificial Sequence
<220> FEATURE:
<223> OTHER INFORMATION: VL-K8

<400> SEQUENCE: 27

Asp Ile Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asn Gly Asn Thr His Leu Asn Trp Tyr Leu Gln Arg Pro Gly Gln Ser
        35                  40                  45

Pro Lys Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Phe Pro Tyr Thr Phe Gly Gly Gly Thr Lys Leu Glu Ile Lys
            100                 105                 110

<210> SEQ ID NO 28
<211> LENGTH: 116
<212> TYPE: PRT
<213> ORGANISM: Artificial Sequence
<220> FEATURE:
<223> OTHER INFORMATION: VH-H8

<400> SEQUENCE: 28

Gln Val Gln Leu Gln Gln Ser Gly Ala Glu Leu Lys Lys Pro Gly Ala
1               5                   10                  15

Ser Val Lys Ile Ser Cys Lys Ala Ser Gly Tyr Thr Leu Ser Ser Tyr
            20                  25                  30

Trp Ile His Trp Val Arg Gln Arg Pro Gly Gln Gly Leu Glu Trp Ile
35 40 45

Gly Glu Ile Leu Pro Gly Ser Gly Ser Thr Asn Tyr Asn Glu Lys Phe
50 55 60

Lys Gly Arg Ala Thr Phe Thr Ala Asp Thr Ser Thr Asn Thr Ala Tyr
65 70 75 80

Met Glu Leu Ser Ser Leu Thr Ser Glu Asp Ser Ala Val Tyr Tyr Cys
85 90 95

Ala Arg Glu Gly Trp Tyr Phe Asp Val Trp Gly Gln Gly Thr Thr Val
100 105 110

Thr Val Ser Ser
115

<210> SEQ ID NO 29
<211> LENGTH: 339
<212> TYPE: DNA
<213> ORGANISM: Artificial Sequence
<220> FEATURE:
<223> OTHER INFORMATION: Synthetic oligonucleotide

<400> SEQUENCE: 29
ctgcagcagt ctggcgctga gctgatgaag cctggggcct cagtgaagat atcctgcaag 60
gctactggct acacactcag tagctactgg ctagagtggg taaagcagag gcctggacat 120
ggccttgagt ggattggaga gattttacct ggaagtggta gtactaacta caatgagaag 180
ttcaagggca aggccacatt cactgcagat acatcctcca acacagccta catgcaactc 240
agcagcctga catctgagga ctctgccgtc tattactgtg caagagaggg ttggtacttc 300
gatgtctggg gcgcagggac cacggtcacc gtctcctca 339

<210> SEQ ID NO 30
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 30
caggttcagc tgcagcagtc tggagctgag ctgatgaagc ctggggcctc agtgaagctt 60
tcctgcaagg ctactggcta cacattcact ggctactgga tagagtgggt aaagcagagg 120
cctggacatg gccttgagtg gattggagag attttacctg gaagtggtag tactaactac 180
aatgagaagt tcaagggcaa ggccacattc actgcagata catcctccaa cacagcctac 240
atgcaactca gcagcctgac aactgaggac tctgccatct attactgtgc aaga 294

<210> SEQ ID NO 31
<211> LENGTH: 113
<212> TYPE: PRT
<213> ORGANISM: Artificial Sequence
<220> FEATURE:
<223> OTHER INFORMATION: Synthetic polypeptide

<400> SEQUENCE: 31

Leu Gln Gln Ser Gly Ala Glu Leu Met Lys Pro Gly Ala Ser Val Lys
1 5 10 15

Leu Ser Cys Lys Ala Thr Gly Tyr Thr Phe Thr Gly Tyr Trp Ile Glu
20 25 30

Trp Val Lys Gln Arg Pro Gly His Gly Leu Glu Trp Ile Gly Glu Ile
35 40 45

```
Leu Pro Gly Ser Gly Ser Thr Asn Tyr Asn Glu Lys Phe Lys Gly Lys
    50                  55                  60

Ala Thr Phe Thr Ala Asp Thr Ser Ser Asn Thr Ala Tyr Met Gln Leu
65                  70                  75                  80

Ser Ser Leu Thr Thr Glu Asp Ser Ala Ile Tyr Tyr Cys Ala Arg Glu
                85                  90                  95

Gly Trp Tyr Phe Asp Val Trp Gly Ala Gly Thr Thr Val Thr Val Ser
            100                 105                 110

Ser
```

<210> SEQ ID NO 32
<211> LENGTH: 293
<212> TYPE: DNA
<213> ORGANISM: Artificial Sequence
<220> FEATURE:
<223> OTHER INFORMATION: Synthetic oligonucleotide

<400> SEQUENCE: 32

```
caggtccagc tgcagcagtc tggagctgag ctggtaaggc ctgggacttc agtgaagatg     60

tcctgcaagg cttctggata caccttcact aattactgga taggttgggc aaagcagagg    120

cctgaacatg gccttgagtg gattggagat atttaccccg gaggtgatta tactaactac    180

aatgagaagt tcaaggacaa ggccacactg actgcagaca aatcctccag cacagcctac    240

atgcagttca gcagcctgac atctgaggac tctgccatct attactgtgc aag           293
```

<210> SEQ ID NO 33
<211> LENGTH: 290
<212> TYPE: DNA
<213> ORGANISM: Artificial Sequence
<220> FEATURE:
<223> OTHER INFORMATION: Synthetic oligonucleotide

<400> SEQUENCE: 33

```
caggtccaac tgcagcagcc tggggctgag cttgtgaagc ctggggcttc agtgaagatg     60

tcctgcaagg cttctggcta caccttcacc agctactgga taacctgggt gaagcagagg    120

cctggacaag gccttgagtg gattggagat atttatcctg gtagtggtag tactaactac    180

aatgagaagt tcaagagcaa ggccacactg actgtagaca aaccctccag cacagcctac    240

atgcagctca gcagcctgac atctgaggac tctgcggtct attattgtgc               290
```

<210> SEQ ID NO 34
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 34

```
caggttcagc tgcagcagtc tggacctgag ctggtgaggc ctggggcttc agtgaagata     60

tcctgcaagg ctcctggcta taccttcacc agccactgga tgcagtgggt aagacagagg    120

cctggacagg gccttgagtg gattggagag atttttcctg gaagtggtag tacttattat    180

aatgagaagt tcaagggcaa ggccacactg actgtagaca catcctccag cacagcctac    240

atgcagctca gcagcctgac atctgaggac tctgcggtct atttctgtgc aaga          294
```

<210> SEQ ID NO 35
<211> LENGTH: 294
<212> TYPE: DNA

<213> ORGANISM: Artificial Sequence
<220> FEATURE:
<223> OTHER INFORMATION: Synthetic oligonucleotide

<400> SEQUENCE: 35
caggtccagc tgaagcagtc tggagctgag ctggtgaagc ctggggcttc agtgaagata 60
tcctgcaagg cttctggcta caccttcact gactactata taaactgggt gaagcagagg 120
cctggacagg gccttgagtg gattggaaag attggtcctg gaagtggtag tacttactac 180
aatgagaagt tcaagggcaa ggccacactg actgcagaca aatcctccag cacagcctac 240
atgcagctca gcagcctgac atctgaggac tctgcagtct atttctgtgc aaga 294

<210> SEQ ID NO 36
<211> LENGTH: 293
<212> TYPE: DNA
<213> ORGANISM: Artificial Sequence
<220> FEATURE:
<223> OTHER INFORMATION: Synthetic oligonucleotide

<400> SEQUENCE: 36
caggtccagc tgcagcagtc tggagctgag ctggtaaggc ctgggacttc agtgaagatg 60
tcctgcaagg cttctggata caccttcact aattactgga taggttgggc aaagcagagg 120
cctgaacatg gccttgagtg gattggagat atttaccccg gaggtgatta tactaactac 180
aatgagaagt tcaaggacaa ggccacactg actgcagaca aatcctccag cacagcctac 240
atgcagttca gcagcctgac atctgaggac tctgccatct attactgtgc aag 293

<210> SEQ ID NO 37
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 37
caggtccagc tgcagcagtc tggagctgag ctggtaaggc ctgggacttc agtgaaggtg 60
tcctgcaagg cttctggata cgccttcact aattacttga tagagtgggt aaagcagagg 120
cctggacagg gccttgagtg gattggagtg attaatcctg gaagtggtgg tactaactac 180
aatgagaagt tcaagggcaa ggcaacactg actgcagaca aatcctccaa cacagcctac 240
atgcagctca gcagcctgac atctgaggac tctgcggtct atttctgtgc aaga 294

<210> SEQ ID NO 38
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 38
caggtccagc tgcagcagtc tggacctgag ctggtgaggc ctggggcttc agtgaagata 60
tcctgcaagg ctcctggcta caccttcacc agccactgga tgcagtgggt aagacagagg 120
cctggacagg gccttgagtg gattggagag atttttcctg gaagtggtag tacttattat 180
aatgagaaat tcaagggcaa ggccacactg actttagaca catcctccag cacagcctac 240
atgcagctca gcagcctgac atctgaagac tctgcggtct atttctgtgc aaga 294

<210> SEQ ID NO 39
<211> LENGTH: 294

<212> TYPE: DNA
<213> ORGANISM: Artificial Sequence
<220> FEATURE:
<223> OTHER INFORMATION: Synthetic oligonucleotide

<400> SEQUENCE: 39
gacgtccaga tccagcagtc tggtgctgag cttgtgaagc ctggggcctc agtgaagctg 60
tcctgcaagg cttctggcta cactttcacc aggtactgga taaactgggt gaagcagagg 120
cctggacaag gccttgagtg gattggaaat atttatcctg gtagtagtcg tactaactac 180
aatgagaagt tcaagaacaa ggccacactg actgtagaca catcctccaa cacagcctac 240
attcagctca ccagcctgac atctgacgac tctgcggtct attattgtgc aaga 294

<210> SEQ ID NO 40
<211> LENGTH: 287
<212> TYPE: DNA
<213> ORGANISM: Artificial Sequence
<220> FEATURE:
<223> OTHER INFORMATION: Synthetic oligonucleotide

<400> SEQUENCE: 40
cagctgcagg agtctggacc cgagctggtg aagcctgggg cttcagtgaa gatctcctgc 60
aaggcttctg gcttcgccct cacaacctcc tatatacact gggtgaagca gaggcctgga 120
cagggacttg agtggattgg atggatttat cctggagctg atgatactaa gtacaatgag 180
aagttcaagg gcaaggccac actgacggca gacacatcct ccagcactgc ctacatacaa 240
ctcagtagtc taacatctga ggactctgcg gtctattact gtgcaag 287

<210> SEQ ID NO 41
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 41
ttcgatgtct ggggcgcagg gaccacggtc accgtctcct ca 42

<210> SEQ ID NO 42
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 42
tacttcgatg tctggggcgc agggaccacg gtcaccgttt cctca 45

<210> SEQ ID NO 43
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 43
tatttcgatg tctggggcac agggaccacg gtcaccgtct cctca 45

<210> SEQ ID NO 44
<211> LENGTH: 98
<212> TYPE: PRT
<213> ORGANISM: Artificial Sequence
<220> FEATURE:

<223> OTHER INFORMATION: Synthetic polypeptide

<400> SEQUENCE: 44

Gln Val Gln Leu Gln Gln Ser Gly Ala Glu Leu Met Lys Pro Gly Ala
1               5                   10                  15

Ser Val Lys Leu Ser Cys Lys Ala Thr Gly Tyr Thr Phe Thr Gly Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg

<210> SEQ ID NO 45
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 45
caggttcagc tgcagcagtc tggagctgag ctgatgaagc ctggggcctc agtgaagctt 60
tcctgcaagg ctactggcta cacattcact ggctactgga tagagtgggt aaagcagagg 120
cctggacatg gccttgagtg gattggagag attttacctg gaagtggtag tactaactac 180
aatgagaagt tcaagggcaa ggccacattc actgcagata catcctccaa cacagcctac 240
atgcaactca gcagcctgac aactgaggac tctgccatct attactgtgc aaga 294

<210> SEQ ID NO 46
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 46
caggtccagc tgcagcagtc tggacctgag ctggtgaggc ctggggcttc agtgaagata 60
tcctgcaagg ctcctggcta caccttcacc agccactgga tgcagtgggt aagacagagg 120
cctggacagg gccttgagtg gattggagag atttttcctg gaagtggtag tacttattat 180
aatgagaaat tcaagggcaa ggccacactg actttagaca catcctccag cacagcctac 240
atgcagctca gcagcctgac atctgaagac tctgcggtct atttctgtgc aaga 294

<210> SEQ ID NO 47
<211> LENGTH: 293
<212> TYPE: DNA
<213> ORGANISM: Artificial Sequence
<220> FEATURE:
<223> OTHER INFORMATION: Synthetic oligonucleotide

<400> SEQUENCE: 47
caggtccagc tgcagcagtc tggagctgag ctggtaaggc ctgggacttc agtgaagatg 60
tcctgcaagg cttctggata caccttcact aattactgga taggttgggc aaagcagagg 120
cctgaacatg gccttgagtg gattggagat atttaccccg gaggtgatta tactaactac 180

```
aatgagaagt tcaaggacaa ggccacactg actgcagaca aatcctccag cacagcctac    240

atgcagttca gcagcctgac atctgaggac tctgccatct attactgtgc aag           293
```

```
<210> SEQ ID NO 48
<211> LENGTH: 293
<212> TYPE: DNA
<213> ORGANISM: Artificial Sequence
<220> FEATURE:
<223> OTHER INFORMATION: Synthetic oligonucleotide

<400> SEQUENCE: 48

caggtccagc tgcagcagtc tggagctgag ctggtaaggc ctgggacttc agtgaagatg     60

tcctgcaagg cttctggata caccttcact aattactgga taggttgggc aaagcagagg    120

cctgaacatg gccttgagtg gattggagat atttaccccg gaggtgatta tactaactac    180

aatgagaagt tcaaggacaa ggccacactg actgcagaca aatcctccag cacagcctac    240

atgcagttca gcagcctgac atctgaggac tctgccatct attactgtgc aag           293
```

```
<210> SEQ ID NO 49
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 49

caggtccagc tgcagcagtc tggagctgag ctggtaaggc ctgggacttc agtgaaggtg     60

tcctgcaagg cttctggata cgccttcact aattacttga tagagtgggt aaagcagagg    120

cctggacagg gccttgagtg gattggagtg attaatcctg gaagtggtgg tactaactac    180

aatgagaagt tcaagggcaa ggcaacactg actgcagaca aatcctccaa cacagcctac    240

atgcagctca gcagcctgac atctgaggac tctgcggtct atttctgtgc aaga          294
```

```
<210> SEQ ID NO 50
<211> LENGTH: 290
<212> TYPE: DNA
<213> ORGANISM: Artificial Sequence
<220> FEATURE:
<223> OTHER INFORMATION: Synthetic oligonucleotide

<400> SEQUENCE: 50

caggtccaac tgcagcagcc tggggctgag cttgtgaagc ctggggcttc agtgaagatg     60

tcctgcaagg cttctggcta caccttcacc agctactgga taacctgggt gaagcagagg    120

cctggacaag gccttgagtg gattggagat atttatcctg gtagtggtag tactaactac    180

aatgagaagt tcaagagcaa ggccacactg actgtagaca aaccctccag cacagcctac    240

atgcagctca gcagcctgac atctgaggac tctgcggtct attattgtgc               290
```

```
<210> SEQ ID NO 51
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 51

gacgtccaga tccagcagtc tggtgctgag cttgtgaagc ctggggcctc agtgaagctg     60

tcctgcaagg cttctggcta cactttcacc aggtactgga taaactgggt gaagcagagg    120
```

```
cctggacaag gccttgagtg gattggaaat atttatcctg gtagtagtcg tactaactac    180

aatgagaagt tcaagaacaa ggccacactg actgtagaca catcctccaa cacagcctac    240

attcagctca ccagcctgac atctgacgac tctgcggtct attattgtgc aaga          294


<210> SEQ ID NO 52
<211> LENGTH: 294
<212> TYPE: DNA
<213> ORGANISM: Artificial Sequence
<220> FEATURE:
<223> OTHER INFORMATION: Synthetic oligonucleotide

<400> SEQUENCE: 52

caggtccagc tgaagcagtc tggagctgag ctggtgaagc ctggggcttc agtgaagata     60

tcctgcaagg cttctggcta caccttcact gactactata taaactgggt gaagcagagg    120

cctggacagg gccttgagtg gattggaaag attggtcctg gaagtggtag tacttactac    180

aatgagaagt tcaagggcaa ggccacactg actgcagaca aatcctccag cacagcctac    240

atgcagctca gcagcctgac atctgaggac tctgcagtct atttctgtgc aaga          294


<210> SEQ ID NO 53
<211> LENGTH: 287
<212> TYPE: DNA
<213> ORGANISM: Artificial Sequence
<220> FEATURE:
<223> OTHER INFORMATION: Synthetic oligonucleotide

<400> SEQUENCE: 53

cagctgcagg agtctggacc cgagctggtg aagcctgggg cttcagtgaa gatctcctgc     60

aaggcttctg gcttcgccct cacaacctcc tatatacact gggtgaagca gaggcctgga    120

cagggacttg agtggattgg atggatttat cctggagctg atgatactaa gtacaatgag    180

aagttcaagg gcaaggccac actgacggca gacacatcct ccagcactgc ctacatacaa    240

ctcagtagtc taacatctga ggactctgcg gtctattact gtgcaag                  287


<210> SEQ ID NO 54
<211> LENGTH: 1008
<212> TYPE: DNA
<213> ORGANISM: Artificial Sequence
<220> FEATURE:
<223> OTHER INFORMATION: Synthetic oligonucleotide

<400> SEQUENCE: 54

gccaaaacaa cacccccatc agtctatcca ctggcccctg ggtgtggagg tacaactggt     60

tcctccgtga ctctgggatg cctggtcaag ggctacttcc ctgagtcagt gactgtgact    120

tggaactctg gatccctgtc cagcagtgtg cacaccttcc cagctctcct gcagtctgga    180

ctctacacta tgagcagctc agtgactgtc ccctccagca cctggccaag tcagaccgtc    240

acctgcagcg ttgctcaccc agccagcagc accacggtgg acaaaaaact tgagcccagc    300

gggcccattt caacaatcaa cccctgtcct ccatgcaagg agtgtcacaa atgcccagct    360

cctaacctcg agggtggacc atccgtcttc atcttccctc caaatatcaa ggatgtactc    420

atgatctccc tgacacccaa ggtcacgtgt gtggtggtgg atgtgagcga ggatgaccca    480

gacgtccaga tcagctggtt tgtgaacaac gtggaagtac acacagctca gacacaaacc    540

catagagagg attacaacag tactatccgg gtggtcagca ccctccccat ccagcaccag    600

gactggatga gtggcaagga gttcaaatgc aaggtcaaca acaaagacct cccatcaccc    660

atcgagagaa ccatctcaaa aattaaaggg ctagtcagag ctccacaagt atacatcttg    720
```

ccgccaccag cagagcagtt gtccaggaaa gatgtcagtc tcacttgcct ggtcgtgggc 780
ttcaaccctg gagacatcag tgtggagtgg accagcaatg ggcatacaga ggagaactac 840
aaggacaccg caccagtcct ggactctgac ggttcttact tcatatatag caagctcaat 900
atgaaaacaa gcaagtggga gaaaacagat tccttctcat gcaacgtgag acacgagggt 960
ctgaaaaatt actacctgaa gaagaccatc tcccggtctc cgggtaaa 1008

<210> SEQ ID NO 55
<211> LENGTH: 337
<212> TYPE: DNA
<213> ORGANISM: Artificial Sequence
<220> FEATURE:
<223> OTHER INFORMATION: Synthetic oligonucleotide

<400> SEQUENCE: 55
gatatcgtga tgacccagtc cccactcact ttgtcggtta ccattggaca accagcctct 60
atctcttgca agtcaagtca gagcctctta tatagtaatg gaaacaccca tttgaattgg 120
ttattacaga ggccaggcca gtctccaaag cgcctaatct atctggtgtc taaactggac 180
tctggagtcc ctgacaggtt cactggcagt ggatcaggaa cagattttac actgaaaatc 240
agcagagtgg aggctgagga tttgggattt tattactgcg tgcaaggtac acattttccg 300
tacacgttcg gagggggac caagctggaa ataaaac 337

<210> SEQ ID NO 56
<211> LENGTH: 302
<212> TYPE: DNA
<213> ORGANISM: Artificial Sequence
<220> FEATURE:
<223> OTHER INFORMATION: Synthetic oligonucleotide

<400> SEQUENCE: 56
gatgttgtga tgacccagac tccactcact ttgtcggtta ccattggaca accagcctct 60
atctcttgca agtcaagtca gagcctctta tatagtaatg gaaaaaccta tttgaattgg 120
ttattacaga ggccaggcca gtctccaaag cgcctaatct atctggtgtc taaactggac 180
tctggagtcc ctgacaggtt cactggcagt ggatcaggaa cagattttac actgaaaatc 240
agcagagtgg aggctgagga tttgggagtt tattactgcg tgcaaggtac acattttcct 300
ca 302

<210> SEQ ID NO 57
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 57

Asp Val Val Met Thr Gln Thr Pro Leu Thr Leu Ser Val Thr Ile Gly
1 5 10 15

Gln Pro Ala Ser Ile Ser Cys Lys Ser Ser Gln Ser Leu Leu Tyr Ser
20 25 30

Asn Gly Lys Thr Tyr Leu Asn Trp Leu Leu Gln Arg Pro Gly Gln Ser
35 40 45

Pro Lys Arg Leu Ile Tyr Leu Val Ser Lys Leu Asp Ser Gly Val Pro
50 55 60

Asp Arg Phe Thr Gly Ser Gly Ser Gly Thr Asp Phe Thr Leu Lys Ile
65 70 75 80

```
Ser Arg Val Glu Ala Glu Asp Leu Gly Val Tyr Tyr Cys Val Gln Gly
                85                  90                  95

Thr His Phe Pro Tyr Thr Phe Gly Gly Gly Thr Lys Leu Glu Ile Lys
            100                 105                 110


<210> SEQ ID NO 58
<211> LENGTH: 301
<212> TYPE: DNA
<213> ORGANISM: Artificial Sequence
<220> FEATURE:
<223> OTHER INFORMATION: Synthetic oligonucleotide

<400> SEQUENCE: 58

gacgttgtga tgacccagac tcaactcact ttgacgatta acattggaca accagcctcc     60

atctcttgca agtcaagtca gagcctctta gatagtgatg gaaagacata tttgaattgg    120

ttgttccaga ggccaggcca gtctccaaag cgcctaatct atctggtgtc taaactggac    180

tctggagtcc ctgacaggtt cactggcagt ggatcaggga cagatttcac actgaaaatc    240

agcagagtgg aggctgagga tttgggagtt tattattgct ggcaaggtac acattttcct    300

c                                                                    301


<210> SEQ ID NO 59
<211> LENGTH: 302
<212> TYPE: DNA
<213> ORGANISM: Artificial Sequence
<220> FEATURE:
<223> OTHER INFORMATION: Synthetic oligonucleotide

<400> SEQUENCE: 59

gatgttgtga tgacccagac tccactcact ttgtcggtta ccattggaca accagcctcc     60

atctcttgca agtcaagtca gagcctctta catagtaatg gaaagacata tttgaattgg    120

ttacaacaga ggcctggcca ggctccaaag cgcctattct atctggtatc caaactggac    180

cctggcatcc ctgacagttt cagtggcagt ggatcagaga cagattttac actgaaaatc    240

agcagagtgg aggctgaaga tttgggagtt tattactgcc tgcaaggtac acattttcct    300

ct                                                                   302


<210> SEQ ID NO 60
<211> LENGTH: 275
<212> TYPE: DNA
<213> ORGANISM: Artificial Sequence
<220> FEATURE:
<223> OTHER INFORMATION: Synthetic oligonucleotide

<400> SEQUENCE: 60

ctgtctttgt cggttaccat tggacaacca gcctctatct cttgcaagtc aagtcagagc     60

ctcttatata gtaatggaaa gacatatttg aattggttac aacagaggcc tggtcaggct    120

ccaaagcacc taatgtatca ggtgtccaaa ctggaccctg gcatccctga caggttcagt    180

ggcagtggat cagaaacaga ttttacactt aaaatcagca gagtggaggc tgaagatttg    240

ggagtttatt actgcttgca aggtacatat tatcc                               275


<210> SEQ ID NO 61
<211> LENGTH: 302
<212> TYPE: DNA
<213> ORGANISM: Artificial Sequence
<220> FEATURE:
<223> OTHER INFORMATION: Synthetic oligonucleotide
```

<400> SEQUENCE: 61
gacgttgtga tgacccagac tccactcact ttatcagcta ccattggaca atcagcctcc 60
gtctcttgca ggtcaagtca gagtctctta catagtaatg gaaacacata cttgaattgg 120
tttgtacaaa ggccaggccc atctccacag cttctaattt atggggtgtt tgaacaggaa 180
tctggggttc ctgacaggtt cagtggcagt gggtctggaa cagatttcac actcaagatc 240
agcagagtgg aggctgagga tttgggagtt tattactgca tgcaagctac ctatgaacct 300
cc 302

<210> SEQ ID NO 62
<211> LENGTH: 301
<212> TYPE: DNA
<213> ORGANISM: Artificial Sequence
<220> FEATURE:
<223> OTHER INFORMATION: Synthetic oligonucleotide

<400> SEQUENCE: 62
gatattttga tgacccaaac tccactctcc ctgcctgtca gtcttggaga tcaagcttcc 60
atctcttgca gatctagtca gagccttgta cacagcaatg gaaacaccta tttatattgg 120
tacctgcaga agccaggcca gtctccaaag ctcctgatct acagggtttc caaccgattt 180
tctggggtcc cagacaggtt cagtggcagt ggatcaggga cagatttcac actcaagatc 240
agcagagtgg aggctgagga tctgggagtt tatttctgct ttcaaggtac acatgttcct 300
c 301

<210> SEQ ID NO 63
<211> LENGTH: 299
<212> TYPE: DNA
<213> ORGANISM: Artificial Sequence
<220> FEATURE:
<223> OTHER INFORMATION: Synthetic oligonucleotide

<400> SEQUENCE: 63
gatgttgtga tgacccaaac tccactctcc ctgtccgtca gtcttggaga tcaagcctcc 60
atctcttgca gatctagtca gagccttgta cacagtaatg gaaacaccta tttacattgg 120
tacctgcaga agccaggcca gtctccaaaa ctcctgatct acaaagtttc cagccgattt 180
tctgggttcc cagacaggtt cagtggcagt ggatccggga cagatttcac actcaagatc 240
agcagagtgg aggctgagga tctgggagtt tatttctgct ctcaaagtac acatgttcc 299

<210> SEQ ID NO 64
<211> LENGTH: 299
<212> TYPE: DNA
<213> ORGANISM: Artificial Sequence
<220> FEATURE:
<223> OTHER INFORMATION: Synthetic oligonucleotide

<400> SEQUENCE: 64
gatgctgtga tgacccaaac tccactctcc ctgcctgtca gtcttggaga tcaagcctcc 60
atctcttgca ggtctagtca gagccttgaa aacagtaatg gaaacaccga tttgaactgg 120
tacctccaga aaccaggcca gtctccacag ctcctgatct acagggtttc caaccgattt 180
tctggggtcc tagacaggtt cagtggtagt ggatcaggga cagatttcac actgaaaatc 240
agcagagtgg aggctgagga tttgggagtt tatttctgcc tccaagttac acatgtcccc 299

<210> SEQ ID NO 65
<211> LENGTH: 299

<212> TYPE: DNA
<213> ORGANISM: Artificial Sequence
<220> FEATURE:
<223> OTHER INFORMATION: Synthetic oligonucleotide

<400> SEQUENCE: 65
gatgttgtga tgacccagac tccactctcc ctgcctgtca gtcttggaga tcaagcctcc 60
atctcttgca gatctagtca gagcattgta catagtaatg gaaacacgta tttagaatgg 120
tacctgcaga aaccaggcca gtctccaaag ctcctgatct acacagtttc caaccgattg 180
tctggggtcc cagacaggtt cagtggcagt ggatcaggga cagacttcac actcaagata 240
agcagagtgg aggctgagga tctgggagtt tattactgct ttcaaggttc acatggtcc 299

<210> SEQ ID NO 66
<211> LENGTH: 299
<212> TYPE: DNA
<213> ORGANISM: Artificial Sequence
<220> FEATURE:
<223> OTHER INFORMATION: Synthetic oligonucleotide

<400> SEQUENCE: 66
gatgttgtga tgacccagac tccactctcc ctgcctgtca gtcttggaga tcaagcctcc 60
atctcttgca gatctagtca gagcattgta catgataatg gaaacaccta tttagagtgg 120
tacctgcaga aacctggcca gtctccaaag ctcctgatct acaaagtttc cagccgattt 180
tctggggtcc cagacaggtt cagtggcagt ggatcaggga cagatttcac actcaagatc 240
agcagagtgg aggctgagga tctgggagtt tattactgct ttcaaggttc acatgttcc 299

<210> SEQ ID NO 67
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 67
tacacgttcg gaggggggac caagctggaa ataaaa 36

<210> SEQ ID NO 68
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 68
acgttcggat cggggaccaa gctggaaata aaa 33

<210> SEQ ID NO 69
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 69
acttttggcc aggggaccaa gttggaaatc aaa 33

<210> SEQ ID NO 70
<211> LENGTH: 100
<212> TYPE: PRT
<213> ORGANISM: Artificial Sequence
<220> FEATURE:

<223> OTHER INFORMATION: Synthetic polypeptide

<400> SEQUENCE: 70

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro
            100

<210> SEQ ID NO 71
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 71

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Leu Ser Ser Tyr
            20                  25                  30

Trp Leu Glu Trp Val Lys Gln Arg Pro Gly His Gly Leu Glu Trp Ile
        35                  40                  45

Gly Glu Ile Leu Pro Gly Ser Gly Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Gly Trp Tyr Phe Asp Val Trp Gly Ala Gly Thr Thr Val
            100                 105                 110

Thr Val Ser Ser
        115

<210> SEQ ID NO 72
<211> LENGTH: 348
<212> TYPE: DNA
<213> ORGANISM: Artificial Sequence
<220> FEATURE:
<223> OTHER INFORMATION: Synthetic oligonucleotide

<400> SEQUENCE: 72
caggtccagc tgcagcagtc tggcgctgag ctgatgaagc ctggggcctc agtgaagata 60
tcctgcaagg ctactggcta cacactcagt agctactggc tagagtgggt aaagcagagg 120
cctggacatg gccttgagtg gattggagag attttacctg gaagtggtag tactaactac 180
aatgagaagt tcaagggcaa ggccacattc actgcagata catcctccaa cacagcctac 240
atgcaactca gcagcctgac atctgaggac tctgccgtct attactgtgc aagagagggt 300
tggtacttcg atgtctgggg cgcagggacc acggtcaccg tctcctca 348

<210> SEQ ID NO 73
<211> LENGTH: 296
<212> TYPE: DNA
<213> ORGANISM: Artificial Sequence
<220> FEATURE:
<223> OTHER INFORMATION: Synthetic oligonucleotide

<400> SEQUENCE: 73
caggtgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc gagaga 296

<210> SEQ ID NO 74
<211> LENGTH: 98
<212> TYPE: PRT
<213> ORGANISM: Artificial Sequence
<220> FEATURE:
<223> OTHER INFORMATION: Synthetic polypeptide

<400> SEQUENCE: 74

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Ile Ile Asn Pro Ser Gly Gly Ser Thr Ser Tyr Ala Gln Lys Phe
50 55 60

Gln Gly Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg

<210> SEQ ID NO 75
<211> LENGTH: 296
<212> TYPE: DNA
<213> ORGANISM: Artificial Sequence
<220> FEATURE:
<223> OTHER INFORMATION: Synthetic oligonucleotide

<400> SEQUENCE: 75
caggtgcagc tggtgcagtc tggggctgag gtgaagaagc ctggggcctc agtgaaggtt 60
tcctgcaagg catctggata caccttcaac agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc gagaga 296

<210> SEQ ID NO 76
<211> LENGTH: 296
<212> TYPE: DNA
<213> ORGANISM: Artificial Sequence
<220> FEATURE:
<223> OTHER INFORMATION: Synthetic oligonucleotide

<400> SEQUENCE: 76
caggtgcagc tggtgcagtc tggggctgag gtgaagaagc ctggggcctc agtgaaggtt 60
tcctgcaagg catctggata caccttcacc agctactata tgcactgggt gcgacaggcc 120
cctggacaag ggcttgagtg gatgggaata atcaacccta gtggtggtag cacaagctac 180
gcacagaagt tccagggcag agtcaccatg accagggaca cgtccacgag cacagtctac 240
atggagctga gcagcctgag atctgaggac acggccgtgt attactgtgc tagaga 296

<210> SEQ ID NO 77
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 77
gggtatagca gcagctggta c 21

<210> SEQ ID NO 78
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 78
gggtatagca gtggctggta c 21

<210> SEQ ID NO 79
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 79
ggtacaactg gaacgac 17

<210> SEQ ID NO 80
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 80
tactactact actacggtat ggacgtctgg ggccaaggga ccacggtcac cgtctcctca 60
g 61

<210> SEQ ID NO 81
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 81
tactactact actactacat ggacgtctgg ggcaaaggga ccacggtcac cgtctcctca 60
g 61

<210> SEQ ID NO 82

<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 82
tactactact actacggtat ggacgtctgg ggcaaaggga ccacggtcac cgtctcctca 60
g 61

<210> SEQ ID NO 83
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 83

Asp Ile Val Met Thr Gln Ser Pro Leu Thr Leu Ser Val Thr Ile Gly
1 5 10 15

Gln Pro Ala Ser Ile Ser Cys Lys Ser Ser Gln Ser Leu Leu Tyr Ser
20 25 30

Asn Gly Asn Thr His Leu Asn Trp Leu Leu Gln Arg Pro Gly Gln Ser
35 40 45

Pro Lys Arg Leu Ile Tyr Leu Val Ser Lys Leu Asp Ser Gly Val Pro
50 55 60

Asp Arg Phe Thr Gly Ser Gly Ser Gly Thr Asp Phe Thr Leu Lys Ile
65 70 75 80

Ser Arg Val Glu Ala Glu Asp Leu Gly Phe Tyr Tyr Cys Val Gln Gly
85 90 95

Thr His Phe Pro Tyr Thr Phe Gly Gly Gly Thr Lys Leu Glu Ile Lys
100 105 110

<210> SEQ ID NO 84
<211> LENGTH: 336
<212> TYPE: DNA
<213> ORGANISM: Artificial Sequence
<220> FEATURE:
<223> OTHER INFORMATION: Synthetic oligonucleotide

<400> SEQUENCE: 84
gatatcgtga tgacccagtc cccactcact ttgtcggtta ccattggaca accagcctct 60
atctcttgca agtcaagtca gagcctctta tatagtaatg gaaacaccca tttgaattgg 120
ttattacaga ggccaggcca gtctccaaag cgcctaatct atctggtgtc taaactggac 180
tctggagtcc ctgacaggtt cactggcagt ggatcaggaa cagattttac actgaaaatc 240
agcagagtgg aggctgagga tttgggattt tattactgcg tgcaaggtac acattttccg 300
tacacgttcg gagggggac caagctggaa ataaaa 336

<210> SEQ ID NO 85
<211> LENGTH: 302
<212> TYPE: DNA
<213> ORGANISM: Artificial Sequence
<220> FEATURE:
<223> OTHER INFORMATION: Synthetic oligonucleotide

<400> SEQUENCE: 85
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggcct 300
cc 302

<210> SEQ ID NO 86
<211> LENGTH: 97
<212> TYPE: PRT
<213> ORGANISM: Artificial Sequence
<220> FEATURE:
<223> OTHER INFORMATION: Synthetic polypeptide

<400> SEQUENCE: 86

Asp Val Val Met Thr Gln Ser Pro Leu Ser Leu Pro Val Thr Leu Gly
1 5 10 15

Gln Pro Ala Ser Ile Ser Cys Arg Ser Ser Gln Ser Leu Val Tyr Ser
20 25 30

Asp Gly Asn Thr Tyr Leu Asn Trp Phe Gln Gln Arg Pro Gly Gln Ser
35 40 45

Pro Arg Arg Leu Ile Tyr Lys Val Ser Asn Arg Asp Ser Gly Val Pro
50 55 60

Asp Arg Phe Ser Gly Ser Gly Ser Gly Thr Asp Phe Thr Leu Lys Ile
65 70 75 80

Ser Arg Val Glu Ala Glu Asp Val Gly Val Tyr Tyr Cys Met Gln Gly
85 90 95

Thr

<210> SEQ ID NO 87
<211> LENGTH: 302
<212> TYPE: DNA
<213> ORGANISM: Artificial Sequence
<220> FEATURE:
<223> OTHER INFORMATION: Synthetic oligonucleotide

<400> SEQUENCE: 87
gatgttgtga tgactcagtc tccactctcc ctgcccgtca cccttggaca gccggcctcc 60
atctcctgca ggtctagtca aagcctcgta cacagtgatg gaaacaccta cttgaattgg 120
tttcagcaga ggccaggcca atctccaagg cgcctaattt ataaggtttc taaccgggac 180
tctggggtcc cagacagatt cagcggcagt gggtcaggca ctgatttcac actgaaaatc 240
agcagggtgg aggctgagga tgttggggtt tattactgca tgcaaggtac acactggcct 300
cc 302

<210> SEQ ID NO 88
<211> LENGTH: 302
<212> TYPE: DNA
<213> ORGANISM: Artificial Sequence
<220> FEATURE:
<223> OTHER INFORMATION: Synthetic oligonucleotide

<400> SEQUENCE: 88
gatgttgtga tgactcagtc tccactctcc ctgcccgtca cccttggaca gccggcctcc 60
atctcctgca ggtctagtca aagcctcgta tacagtgatg gaaacaccta cttgaattgg 120
tttcagcaga ggccaggcca atctccaagg cgcctaattt ataaggtttc taactgggac 180
tctggggtcc cagacagatt cagcggcagt gggtcaggca ctgatttcac actgaaaatc 240
agcagggtgg aggctgagga tgttggggtt tattactgca tgcaaggtac acactggcct 300

```
cc                                                                  302


<210> SEQ ID NO 89
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 89

ctcacgttcg gcggagggac caaggtggag atcaaa                              36


<210> SEQ ID NO 90
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 90

ctcactttcg gcggagggac caaggtggag atcaaac                             37


<210> SEQ ID NO 91
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 91

tacacttttg gccaggggac caagctggag atcaaac                             37


<210> SEQ ID NO 92
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 92

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Thr Tyr
            20                  25                  30

Tyr Leu His Trp Val Arg Gln Ala Pro Gly Gln Gly Leu Glu Trp Met
        35                  40                  45

Gly Trp Ile Tyr Pro Gly Asn Gly His Ala Gln Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Glu Gly Phe Asp Tyr Trp Gly Gln Gly Thr Thr Val
            100                 105                 110

Thr Val Ser Ser
        115


<210> SEQ ID NO 93
<211> LENGTH: 117
<212> TYPE: PRT
<213> ORGANISM: Artificial Sequence
<220> FEATURE:
```

<223> OTHER INFORMATION: Synthetic polypeptide

<400> SEQUENCE: 93

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ser Ile Ile Pro Trp Phe Gly Thr Thr Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Ser Glu Tyr Tyr Phe Asp His Trp Gly Gln Gly Thr Leu
            100                 105                 110

Val Thr Val Ser Ser
        115

<210> SEQ ID NO 94
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 94

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Tyr Ile Asn Trp Val Arg Gln Ala Pro Gly Gln Gly Leu Glu Trp Met
        35                  40                  45

Gly Thr Ile Asn Pro Val Ser Gly Ser Thr Ser Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Trp Phe Asp Tyr Trp Gly Gln Gly Thr Leu Val Thr
            100                 105                 110

Val Ser Ser
        115

<210> SEQ ID NO 95
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Ser Ser Tyr
            20                  25                  30

Trp Ile His Trp Val Arg Gln Ala Pro Gly Gln Gly Leu Glu Trp Met

```
        35                  40                  45

Gly Trp Ile Leu Pro Gly Ser Gly Ser Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Trp Tyr Phe Asp Val Trp Gly Gln Gly Thr Leu Val
            100                 105                 110

Thr Val Ser Ser
        115


<210> SEQ ID NO 96
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 96

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Glu Ser
            20                  25                  30

Asp Gly Lys Thr Tyr Leu Asn Trp Tyr Leu Gln Lys Pro Gly Gln Ser
        35                  40                  45

Pro Gln Leu Leu Ile Tyr Leu Val Ser Ile Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Ala
                85                  90                  95

Thr His Phe Pro Gln Thr Phe Gly Gly Gly Thr Lys Val Glu Ile Lys
            100                 105                 110


<210> SEQ ID NO 97
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 97

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Pro Thr Phe Gly Gly Gly Thr Lys Val Glu Ile Lys
            100                 105                 110
```

-continued

```
<210> SEQ ID NO 98
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 98

Asp Ile Val Met Thr Gln Ser Pro Leu Ser Leu Ser Val Thr Pro Gly
1               5                   10                  15

Glu Pro Ala Ser Ile Ser Cys Arg Ser Ser Gln Ser Leu Leu His Thr
            20                  25                  30

Asn Gly Tyr Asn Tyr Leu Asp Trp Tyr Val Gln Lys Pro Gly Gln Ser
        35                  40                  45

Pro Gln Leu Leu Ile Tyr Leu Ala Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Val Tyr Tyr Cys Met Gln Ala
                85                  90                  95

Leu Gln Ile Pro Arg Thr Phe Gly Gln Gly Thr Lys Val Glu Ile Lys
            100                 105                 110


<210> SEQ ID NO 99
<211> LENGTH: 112
<212> TYPE: PRT
<213> ORGANISM: Artificial Sequence
<220> FEATURE:
<223> OTHER INFORMATION: Synthetic polypeptide

<400> SEQUENCE: 99

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Leu Tyr Ser
            20                  25                  30

Asn Gly Asn Thr His Leu Asn Trp Tyr Leu Gln Lys Pro Gly Gln Ser
        35                  40                  45

Pro Gln Leu Leu Ile Tyr Leu Val Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Tyr Thr Phe Gly Gly Gly Thr Lys Val Glu Ile Lys
            100                 105                 110
```